(12) United States Patent
Garver et al.

(10) Patent No.: US 6,916,490 B1
(45) Date of Patent: Jul. 12, 2005

(54) CONTROLLED RELEASE OF BIOACTIVE SUBSTANCES

(75) Inventors: Robert I. Garver, Hoover, AL (US); Subramanian Kalyanasundaram, Gaithersburg, MD (US); Kam W. Leong, Ellicott City, MD (US)

(73) Assignees: UAB Research Center; The Johns Hopkins University

( * ) Notice: Subject to any disclaimer, the term of this patent is extended or adjusted under 35 U.S.C. 154(b) by 0 days.

(21) Appl. No.: 09/359,593

(22) Filed: Jul. 23, 1999

Related U.S. Application Data

(60) Provisional application No. 60/093,946, filed on Jul. 23, 1998.

(51) Int. Cl.$^7$ .......................... A61K 9/14; A01N 63/00; C12N 15/63; C12N 15/00
(52) U.S. Cl. ..................... 424/489; 424/93.1; 424/93.2; 435/455; 435/320.1
(58) Field of Search .............................. 435/455, 456, 435/458, 320.1, 440; 424/489, 491, 493, 496, 93.1, 93.2; 514/44

(56) References Cited

U.S. PATENT DOCUMENTS

| | | | |
|---|---|---|---|
| 4,325,937 A | * 4/1982 | Spence et al. ................. 424/16 |
| 4,376,113 A | 3/1983 | Suglia et al. | |
| 4,741,872 A | 5/1988 | De Luca et al. ............. 264/4.7 |
| 4,818,542 A | 4/1989 | DeLuca et al. ............. 424/491 |
| 5,407,609 A | 4/1995 | Tice et al. ..................... 264/46 |
| 5,531,925 A | 7/1996 | Landh et al. .......... 252/299.01 |
| 5,580,859 A | 12/1996 | Felgner et al. ................ 514/44 |
| 5,626,863 A | 5/1997 | Hubbell et al. ............. 424/426 |
| 5,759,582 A | 6/1998 | Leong et al. ............... 424/492 |
| 5,783,567 A | 7/1998 | Hedley et al. ................ 414/44 |
| 5,861,159 A | 1/1999 | Pardoll et al. | |
| 5,942,253 A | * 8/1999 | Gombotz et al. ........... 424/501 |
| 5,972,707 A | * 10/1999 | Roy et al. .................... 435/455 |
| 6,008,202 A | 12/1999 | Huang et al. | |
| 6,025,337 A | * 2/2000 | Truong et al. ................ 514/44 |
| 6,159,502 A | * 12/2000 | Russell-Jones et al. ..... 424/489 |

FOREIGN PATENT DOCUMENTS

| | | |
|---|---|---|
| EP | 248 531 A2 | 12/1987 |
| EP | 467 389 A2 | 1/1992 |
| EP | 467 389 A3 | 1/1992 |
| EP | 635 261 B1 | 1/1995 |
| WO | WO 94/23699 | 10/1994 |
| WO | WO 94/23738 | 10/1994 |
| WO | WO 95/03789 | 2/1995 |
| WO | WO 95/20660 | 8/1995 |
| WO | WO 95/24929 | 9/1995 |
| WO | WO 95/35097 | 12/1995 |
| WO | WO 96/00295 | 1/1996 |
| WO | WO 96 026 55 A1 | 2/1996 |
| WO | WO 96/29998 | 10/1996 |
| WO | WO 98/01162 | 1/1998 |
| WO | WO 98/30207 | 7/1998 |

OTHER PUBLICATIONS

Leitner, W. et al.; DNA and RNA–based vaccines: principles, progress and prospects, 2000, Vaccine 18: 765–777.*

McCluskie, M. et.al.; Routeand method of delivery olf DNA vaccine inf.luence immune responses in mice and non–human primates, 1999I Mol. Med. 5: 287–300.*

Casey, G. et.al.; Growth suppression of human breast cancer cells by the introduction of a wild–type p53 gene; 1991. Oncogene 6: 1791–1797.*

Miller, N. et al.; Targeted vectors for gene therapy, 1995, FASEB J. 9: 190–199.*

Deonarian. M.; Ligand–targeted receptor–mediated vectors for gene therapy, 1998, Exp. Opin. Ther. Patents 8: 53–69.*

Verma, I.; Gene therapy–promises. problems and prospects, 1997; Nature 389: 239–242.*

Chattergoon, M.: Genetic immunization: a new era in vaccines and immune therapeutics. 1997: FASEB J. 11: 753–763.*

Narayani & Rao. J. Biomater. Sci. Polymer Edn. 7:39–48, 1995.*

Kalyanasundaram et al. Cancer gene therapy 4:S23, 1997.*

Kalyanasundaram et al. Cancer gene therapy 6:107–112, 1999.*

Beer et al. Adv. drug delivery reviews 27:59–66, 1997.*

Dang et al. Clin. Cancer Res. 5:471–474, 1999.*

Wivel & Wilson. Hematol. Oncol. Clin. North Am. 12:483–501, 1998.*

Eck & Wilson. Gene–based therapy in Goodman & Gilman's The pharmacological basis of therapeutics, Ninth edition, pp. 77–101, 1996.*

Leong et al. J. Controlled Rel. 53: 183–193, 1998.*

Kalyanasundaram et al., "Coacervate microspheres as carriers of recombinant adenoviruses," Cancer Gene Therapy, 6:(2)107–112 (1999).

Kalyanasundram et al., "Recombinant adenovirus can be encapsulated and released from coacervate microspheres in a time–dependent fashion," Cancer Gene Therapy, 4(6) S23 (1997), Abstract.

(Continued)

Primary Examiner—David Guzo
Assistant Examiner—Quang Nguyen
(74) Attorney, Agent, or Firm—Gillian M. Fenton, Esq.; Foley Hoag LLP

(57) ABSTRACT

The present invention contemplates in part coacervates in which a bioactive substance and delivery agent are encapsulated therein for controlled release. In certain embodiments, said bioactive substance and delivery agent are a viral vector and virus, respectively. Processes for preparing and using coacervates of the present invention are described.

41 Claims, No Drawings

OTHER PUBLICATIONS

Alpar et al., "Potential of Particulate Carrier for the Mucosal Delivery of DNA Vaccines". Biochemical Society Transactions 25(2): 347 (1997).

Heard, R. "HLA and Autoimmune Disease", HLA & Disease, pp. 123–151 (1994).

Leong et al., "Polymeric Controlled Drug Delivery", Advanced Drug Delivery Reviews. 199–233 (1987).

O'Hagan, Derek T., "Recent Advances in Vaccine Adjuvants for Systemic and Mucosal Administration", J. Pharm. Pharmacol. 49: 1–10 (Sep. 15, 1997).

Tomlinson et al., "Controllable Gene Therapy Pharmaceutics of non-viral Gene Delivery Systems", Journal of Controlled Release 39: 357–372 (1996).

Weiner et al., "Genetics Vaccines", Scientific American pp. 50–57 (Jul. 1999).

Hedley, M. Genetic Modulation of Antigen Presentation, MHC Molecules: Expression Assembly and Function, Ch. 17, pp. 281–293: Editors: Robert G. Urban and Roman M. Chicz: Published by R. G. Landes & Co. (1996).

* cited by examiner

CONTROLLED RELEASE OF BIOACTIVE SUBSTANCES

RELATED APPLICATION INFORMATION

This Application claims the benefit of priority under 35 U.S.C. § 119(c) to Provisional Application 60/093,946, filed Jul. 23, 1998, the specification of which is incorporated by reference in its entirety.

ACKNOWLEDGEMENT OF GOVERNMENT RIGHTS

The present invention was made in part with support from the U.S. Government under a grant from the National Institutes of Health. The U.S. Government has certain rights in this invention.

INTRODUCTION

The effectiveness of gene therapy is limited in part by the delivery systems used to administer the gene of interest. In general, gene therapy involves the transfer of genetic material into the cells of a patient to provide expression of delivered genes. However, the development of clinical applications of gene therapy has been limited by, among other things, inefficient gene transfer, transient expression, immune rejection, and cytotoxicity. Such a result is not entirely unexpected, because many of the steps required for gene therapy, including cell membrane penetration, intracellular trafficking and nuclear entry of genes, are incompletely understood.

One means of addressing some of these issues involves the use of recombinant viruses. However, the therapeutic utility of recombinant viruses, in particular of adenoviruses, is limited in part by difficulties in directing the viruses to specific sites, and by the requirement for bolus administration, both of which limit the efficiency of target tissue infection. Recombinant adenovirus has emerged as a leading vector for the delivery of new genes to mammalian cells. Advantages include the extensive understanding of the virus biology, well-established methods for the generation of high titer recombinant adenoviruses, and generally high expression of the viral transgene, among others (Curiel et al., *Gene Therapy for Diseases of the Lung* 104:29–52). Two important limitations of the existent adenoviral vectors are the inability to achieve (i) targeted delivery of the recombinant adenoviruses by systemic administration, and (ii) extended, local exposure to the adenovirus without the requirement for frequent redosing.

With respect to the targeting problem, efforts to develop a targeted adenovirus have focused on direct modification of the adenovirus exterior. Since the knob portion of the adenoviral fiber binds to the adenoviral receptor, the leading efforts in adenoviral retargeting have focused on modifying the fiber knob. Louis et al., *Journal of Virology* 68:4104–4106 (1994); Stevenson et al., *Journal of Virology* 69:2850–2857 (1995); Lieberman et al., *Virus Research* 45:1 111–121 (1996); Krasnykh et al., *Journal of Virology* 70:6839–6847 (1996); Wickham et al., *Journal of Virology* 70:6831–6838 (1996); Douglas et al., *Nature Biotechnology* 14:1574–1578 (1996); Wickham et al., *Nature Biotechnology* 14:1570–1573 (1996).

Coacervation is a process of separation of colloidal solutions into two or more immiscible liquid phases. When oppositely charged polyelectrolytes are brought into contact with one another, a spontaneous phase separation may occur with the resultant formation of coacervates. The coacervate is the phase in which colloids are concentrated. Coacervation has been employed to encapsulate biologically active substances. For example, U.S. Pat. No. 4,794,000 describes a method for preparing a pharmaceutical composition for oral administration based on a two phase coacervate system in which erythromycin is included as the active ingredient. U.S. Pat. No. 5,051,304 describes microcapsules formed by coacervation between gelatin and a chemically depolymerized polysaccharide.

The present invention, in one aspect, contemplates preparing and using coacervates having recombinant viruses encapsulated therein. In certain embodiments, the coacervates of the present invention, and methods of using the same, may allow for a sustained release of recombinant virus particles for gene therapy.

SUMMARY OF THE INVENTION

The present invention contemplates coacervates, and methods of making and using the same, that may be used to deliver bioactive substances, including for example proteins, peptides, genes, nucleic acids and viral vectors containing transgenes. In certain embodiments, the coacervates are in the form of microspheres. Certain embodiments of the present invention, including coacervates and methods of using them, may deliver a recombinant virus particle containing a transgenic in a controlled release manner for gene transfer applications and gene therapy. In certain embodiments, a delivery agent may be encapsulated in the coacervate to facilitate the intracellular delivery of any bioactive substance.

The coacervates and gene delivery systems of the present invention, and methods of using the same, have a variety of desirable features, some of which may be present in certain embodiments of the invention: (i) a single dose may be sufficient to achieve the desired therapeutically beneficial response through sustained release of the bioactive substance; (ii) to targeting molecules may be conjugated to the coacervate for potential tissue targeting and, if applicable to the dimensions of the coacervate, to stimulate receptor-mediated endocytosis; (iii) bioavailability of bioactive substances, including nucleic acids, may be improved because of protection attributable to the coacervate from serum nuclease degradation and other undesirable reactions; (iv) other bioactive substances and other materials, including for example delivery agents, may be co-encapsulated in the coacervates; and (v) the coacervates may be lyophilized to retain their bioactivity.

In another aspect, the coacervates of the present invention, and methods of using the same may be used to effect DNA vaccination, whereby the bioactive substance is a nucleic acid that expresses an antigen to provoke an immunogenic response in the host. In still another aspect, the coacervates of the present invention, and methods of using the same, may be used in diagnostic applications.

In part, this invention describes the synthesis of coacervate microspheres that can be used to deliver bioactive substances, including bioactive proteins, peptides, genes, nucleic acids or viral vectors containing transgenes, to a target site. The microspheres of the invention are particularly useful for delivering a recombinant virus containing a transgene to a target site in a controlled release manner for gene transfer applications.

In certain embodiments, the present invention contemplates bioactive substances incorporated in coacervate microspheres. In certain embodiments, the microspheres comprise gelatin and alginate stabilized with calcium ions.

In one embodiment, the viruses comprise viruses which have been engineered to be used as vectors for delivery of genes in vivo. In a other embodiments, the virus comprises a recombinant adenovirus containing a transgene to be delivered to a site in vivo; however, other recombinant or engineered naturally occurring viruses may be used as vectors in the present invention.

In one aspect, the invention comprises a gene delivery system comprising a virus which has engineered to contain a transgene incorporated in coacervate microspheres. The gene delivery system of the invention provides controlled or sustained release of the viral vector into the target site, thereby permitting transfection of the target tissue with the transgene.

In one embodiment of the present invention, the virus, alginate and gelatin are combined under conditions sufficient to form microspheres incorporating the virus. The resulting microspheres permit controlled release of the incorporated virus over time. Ultra structural evaluation shoved the microspheres formed in this fashion were approximately 0.8 $\mu M$ to 10 $\mu M$ in diameter with viruses substantially evenly distributed throughout.

In certain embodiments, coacervate microspheres according to the invention may be used to encapsulate, and release in a time-dependent fashion, bioactive virus particles. In experiments described below, the microspheres according to the invention achieved sustained release of virus with a nominal loss of bioactivity. The pattern of release and total amount of virus released may be modified by changes in microsphere formulation. Administration of adenovirus-containing microspheres to human tumor nodules engrafted in mice showed that the viral transgene was transferred to the tumor cells.

In one aspect, microspheres of the present invention may be used as a carrier for the virus for targeting the virus in vivo. The in vivo biodistribution of microspheres may be modified, for example, by altering the size of the microspheres, or by the attachment of targeting moieties to the microsphere exterior, without requiring any modification of the encapsulated virus. In addition, microspheres of the present invention may be manipulated to modulate the rate of virus release at the target site. The present microsphere carriers also may be used to co-deliver the virus and additional molecules or compounds. For example, molecules that are useful for amplifying viral transgene expression.

In certain embodiments, the present invention contemplates a gene delivery system including the following: (i) a nucleic acid sequence encoding a sequence of interest, and (ii) a delivery agent for facilitating intracellular delivery of the nucleic acid. In certain embodiments, the nucleic acid may be operably linked to a regulatory element to cause expression of such sequence. In other embodiments, such nucleic acid sequence may be a transgene. In certain embodiments, the delivery agent may be a viral vector, such as an adenoviral vector, an adeno-associated viral vector or a retroviral vector. In such embodiments, the virus or virus particle serves as a delivery agent. For in vivo delivery to a mammal, such as a human the gene delivery system may further include a pharmaceutically acceptable carrier for administration to an animal. In certain embodiments, coacervates of the present invention, pharmaceutical formulations of such coacervates, and the like are sterile and/or nonpyrogenic.

In certain embodiments, the delivery agent is a molecule that facilitates the intracellular delivery of transfer vectors and other nucleic acids containing the nucleic acid sequence of interest. Some examples of such delivery agents include sterols and lipids.

In one aspect, the coacervates of the present invention may be lyophilized. The lyophilized coacervates exhibit greater retention of bioactivity for any bioactive substance encapsulated therein, and are readily rehydrated for use.

In another aspect, the coacervates of the present invention may be used in the manufacture of a medicament for any number of uses, including for example treating any disease or other treatable condition of a patient. In still other aspects, the present invention is directed to a method for formulating coacervates of the present invention in a pharmaceutically acceptable carrier.

In other embodiments, this invention contemplates a kit including coacervates of the present invention, and optionally instructions for their use. Uses for such kits include, for example, imaging, diagnosis, therapy, vaccination, and other applications. In certain embodiments, the coacervates of the kit have been lyophilized and require hydration before use.

The practice of the present invention may employ in part, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transportation And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

DETAILED DESCRIPTION OF THE INVENTION

1. Definitions

For convenience, before further description of the present invention, certain terms and phrases employed in the specification, examples, and appended claims are collected here. These definitions should be read in light of the rest of the disclosure and be understood as by a person of skill in the art.

The term "antisense" nucleic acid refers to oligonucleotides which specifically hybridize (e.g. bind) under cellular conditions with a gene sequence, such as at the cellular mRNA and/or genomic DNA level, so as to inhibit expression of that gene, e.g. by inhibiting transcription and/or translation. The binding may be by conventional base pair complementarily, or, for example, in the case of binding to DNA duplexes, through specific interactions in the major groove of the double helix.

The terms "bioactive substance" and "pharmaceutically active substance" are intended to encompass any substance that will produce a therapeutically beneficial response when administered to a host, both human and animal, e.g., the substance may be used as part of a prophylatic or therapeutic treatment. Suitable substances include, but are not restricted to analgesics, antibacterials, antifungals, immunosuppressants, anti-inflammatories, nucleic acids, antigens, anti-cancer agents, enzymes, organic catalysts, ribozymes, organometallics, proteins, glycoproteins, polyamino acids, antibodies, steroidal molecules, antibodies, antimycotics, cytokines, oleophobics, pharmaceuticals, and therapeutics. Some non-limiting examples of antibacterials include penicillins, cephalosporins, tetracyclines, quinolones, and aminoglycosides. Representatives of anti-inflammatories include hydrocortisone, colchicine, ibuprofen, indomethacin, and piroxicam. In addition, biological entities, such as viruses, virenos, and prions are considered bioactive substances. The active substances may be water-soluble or water-insoluble and may include those having a high molecular weight, such as proteins, peptides, carbohydrates and glycoproteins. In certain embodiments of the present invention, the bioactive substance comprises a transgene. The transgene may be delivered to the target site using a transfer vector. Viral vectors are particularly effective for this purpose. The microspheres of the present invention are particularly suitable for the targeted delivery and sustained release of viral vectors containing a transgene for gene therapy purposes.

One type of bioactive substance contemplated by the present invention is a "transgene." A transgene may be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genomic in such a way as to alter the genome of the cell into which it is inserted (e.g., it is inserted at a location which differs from that of the natural gene or its insertion results in a knockout). A transgene may also be present in a cell in the form of an episome. A transgene may include one or more regulatory elements and any other nucleic acid, such as introns, that may be necessary for optimal expression of a selected nucleic acid. In certain embodiments, a transgene comprises a nucleic acid sequence of interest and one or more regulatory elements for controlling transcription of the nucleotide sequence encoded by such nucleic acid sequence, e.g., the regulatory element is operably linked to a nucleic acid.

In certain embodiments, the transgene or other bioactive substance may be a "gene therapy construct," which is an expression vector which may alter the phenotype of a cell when taken up by the cell, or a gene construct. In certain embodiments, the gene therapy construct may be an "recombinant coding sequence" which encodes a polypeptide, or is transcribable to an antisense nucleic acid, a ribozyme, or any other RNA product which alters the phenotype of the cell in which it is produced. "Recombinant gene" refers to a genetic construct including a "recombinant coding sequence."

The term "biocompatibility" or "biocompatible" when used in relation to coacervates of the present invention refers to coacervates that are neither themselves toxic to the host (e.g., an animal or human), nor degrade (if at all) at a rate that produces byproducts at toxic concentrations in the host. To determine whether any subject coacervates are biocompatible, it may be necessary to conduct a toxicity analysis. Such assays are well known in the art. On example of such an assay would be performed with live carcinoma cells, such as GT3TKB tumor cells, in the following manner: the sample coacervate is degraded in 1M NaOH at 37° C. until complete degradation is observed. The solution is then neutralized with 1M HCl. About 200 $\mu$L of various concentrations of the degraded coacervate products are placed in 96-well tissue culture plates and seeded with human gastric carcinoma cells (GT3TKB) at $10^4$/well density. The degraded coacervate products are incubated with the GT3TKB cells for 48 hours. The results of the assay may be plotted as % relative growth vs. concentration of degraded coacervate in the tissue-culture well. In addition, polymers and formulations of the present invention may also be evaluated by well-known in vivo tests, such as subcutaneous implantations in rats to confirm that they hydrolyze without significant levels of irritation or inflammation at the subcutaneous implantation sites.

The term "biodegradable" refers to those embodiments in which coacervates of the present invention are intended to degrade during use. In general, degradation attributable to biodegradability involves the degradation of a coacervate into its constituents and encapsulated materials. The degradation rate of a biodegradable coacervate often depends in part on a variety of factors, including the identity of any constituents that form the coacervate and their ratio, the identity and loading of any material (including bioactive substance and delivery agent encapsulated in a coacervate), how any coacervate may be crosslinked and to what extent. For example, a coacervate that is crosslinked will, in all likelihood, degrade more slowly than one that is not crosslinked.

When used with respect to the bioactive substance, the term "controlled release" is intended to mean that the present comparison releases the bioactive substance over time in contrast to a bonus type administration in which the entire amount of the bioactive substance is presented to the target at one time. The release will vary as explained below.

The term "delivery agent" refers to a molecule that facilitates the intracellular delivery of a bioactive substance. Examples of delivery agents include: sterols (e.g. cholesterol), lipids (e.g. a cat ionic lipid, virosome or liposome), viruses (e.g. adenovirus, adeno-associated virus, and retrovirus) or target cell specific binding agents (e.g. ligands recognized by target cell specific receptors). In certain embodiments, when the bioactive substance is a nucleic acid, such as a transgene, the delivery agent may be a viral vector. In such embodiments, the delivery agent comprises a virus or virus particle that has been engineered to contain the nucleic acid. Other delivery agents contemplated by the present invention are discussed in greater detail below.

The term "$ED_{50}$" means the dose of a drug or other material, including for example a gene delivery system of the present invention, which produces 50% of its maximum response or effect. Alternatively, "$ED_{50}$" means the dose which produces a pre-determined response in 50% of test subjects or preparations. The term "$LD_{50}$" means the dose of a drug or other material, including for example a gene delivery system of the present invention, which is lethal in 50% of test subjects. The term "therapeutic index" refers to the therapeutic index of a drug defined as $ED_{50}/LD_{50}$.

The term "gene" or "recombinant gene" refers to a nucleic acid comprising an open reading frame encoding a polypeptide, including both exonic and (optionally) intronic sequences.

The term "gene construct" refers to a vector, plasmid, viral genome or the like which includes an "coding sequence" for a polypeptide or which is otherwise transcribable to a biologically active RNA (e.g., antisense, decoy, ribozyme, etc), can transfect cells, preferably mammalian cells, and can cause expression of the coding sequence in cells transfected with the construct. The gene construct may include one or more regulatory elements operably linked to the coding sequence, as well as intronic sequences, poly adenylation sites, origins of replication, marker genes, etc.

The term "gene delivery system" refers to encapsulating in a coacervate the following: (i) a nucleic acid sequence encoding a sequence of interest, and (ii) a delivery agent for facilitating intracellular delivery of the nucleic acid. In certain embodiments, the nucleic acid may be operably linked to a regulatory element. In other embodiments, such nucleic acid sequence may be a transgene. In certain embodiments, the delivery agent may be a viral vector, such as an adenoviral vector, an adeno-associated viral vector or a retroviral vector.

The term "genetic immunization" generally refers to the delivery of nucleic acid, including DNA or RNA sequences, to tissues in vivo in order provoke the production of proteins which, if seen by the host as foreign, may induce an immune response.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "host cell" or "target cell" refers to a cell transduced with a specified transfer vector. The cell is optionally selected from in vitro cells such as those derived from cell culture, ex vivo cells, such as those derived from an organism, and in vivo cells, such as those in an organism.

The term "incorporated" or "encapsulation," when used in reference to a bioactive substance or other material and a coacervate, denotes formulating a bioactive substance or other material into a coacervate useful for controlled release of such substance or material. As used herein, those terms contemplate any manner by which a bioactive substance is incorporated into a coacervate, including for example: distributed throughout the matrix, appended to the surface of the matrix, and encapsulated inside the matrix. The term "coincorporation" or "coencapsulation" as used herein refers to the incorporation of an bioactive substance in a coacervate and at least another bioactive substance or other material.

The term "microspheres" refers to substantially spherical colloidal structures having a bioactive substance incorporated therein formed by a coacervation process. The microspheres generally have a matrix-type structure, and the bioactive substance is distributed within the matrix. The microspheres generally have a size distribution within the range of from about 0.5 $\mu$M to about 100 $\mu$M. In certain embodiments of the present invention, over 90% of the microspheres formed in a single preparation of coacervates have a diameter in excess of about 5 $\mu$M. Other sizes are also contemplated by the invention. In general, "microcapsules" may be distinguished from microspheres, because microcapsules are genetically described as structures in which a substrate, such as a bioactive agent, is covered by a coating of some type. The term "microparticle" may be used to describe constructs which cannot be readily placed into either of the above two categories or as a generic term for both. If the constructs are less than one micron in diameter, then the corresponding terms "nanosphere," "nanocapsule," may be utilized. A microsphere formed by coacervation is one example of a coacervate.

When a large number of microspheres are collected in a coacervate composition, they may have a variable particle size. In certain embodiments, the particle size distribution may to be uniform, e.g., within less than about a 20% standard deviation of the median volume diameter, and in other embodiments, still more uniform or within about 10% of the median volume diameter.

The term "modulation" refers to both up regulation (i.e., activation or stimulation) and down regulation (i.e., inhibition or suppression) of a response.

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides. Exemplary nucleic acids for use in the subject invention include antisense, decoy molecules, recombinant genes (including transgenes) and the like.

"Operably linked" when describing the relationship between two nucleic acid regions means that they are functionally related to each other. For example, a promoter or other regulatory element is operably linked to a coding sequence of DNA if it controls the transcription of the coding sequence.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal and intrasternal injection and infusion.

A "patient," "subject" or "host" to be treated by the subject method may mean either a human or non-human animal.

The phrase "pharmaceutically acceptable" refers to those coacervates and dosages thereof within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "prophylactic or therapeutic" treatment refers to administration to the host of the subject microspheres. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish or ameliorate the existing unwanted condition or side effects therefrom).

The terms "protein," "polypeptide" and "peptide" are used interchangeably when referring to a gene product.

"Recombinant host cells" refers to cells which have been transformed or transfected with vectors constructed using recombinant DNA techniques.

The terms "recombinant protein," "heterologous protein" and "exogenous protein" are used interchangeably to refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

"Regulatory element" is a generic term used to refer to nucleotide sequences (such as DNA sequences) that induce or control transcription of protein coding sequences with which they are operably linked. Examples of regulatory elements categorized by function include initiation signals, enhancers, promoters and the like. Exemplary regulatory elements are described in Goeddel; *Methods in Enzymology* 185 (1990). In certain embodiments, transcription of a gene or other DNA is under the control of a promoter sequence (or other regulatory element) which controls the expression of a coding sequence in a cell-type in which expression is intended. A variety of promoters categorized by function are known. The term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well. The term "inducible" promoter refers to a promoter which is under environmental or developmental regulation. The term "constitutive" promoter refers to a promoter which is active under most environmental and developmental conditions.

Other examples of regulatory elements include the following: the early and late promoters of SV40, adenovirus or cytomegalovirus; immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the *baculovirus* system and other sequences known to control the expression of genes of prokaryotic or eukaryotic cells or their viruses, and various combinations thereof.

A "ribozyme sequence" is a catalytic RNA sequence capable of cleaving a target RNA, such as a hairpin or hammerhead ribozyme. The term also encompasses a nucleic acid sequence in an expression cassette from which the RNA is transcribed.

The phrases "systemic administration," "administered systematically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

The phrase "therapeutically effective amount" means that amount of a bioactive substance that, when present in a coacervate of the present invention, produces some desired effect at a reasonable benefit/risk ratio applicable to any medical treatment. In certain embodiments, a therapeutically effective amount of a bioactive substance for in vivo use will likely depend on a number of factors, including: the rate of release of the bioactive substance from the coacervate, which will depend in part on the chemical and physical characteristics of the such coacervate, the identity of the bioactive substance, the mode and method of administration; any other materials incorporated in the coacervate in addition to the bioactive substance. When the pharmaceutically active substance comprises a nucleic acid, expression vector or the like, the therapeutically effective amount may depend on a number of other variables, including the rate at which such substance gains access to the nucleus of a host cell (with or without the assistance of a delivery agent).

The term "transfection" means the introduction of a nucleic acid, e.g., an expression vector, into a recipient cell, which in certain embodiments may be by nucleic acid-mediated gene transfer. "Transformation," as used with respect to transfected nucleic acid, refers to a process in which a cell's genotype is changed as a result of the cellular uptake of exogenous nucleic acid.

The term "transfer vector" refers to a first nucleic acid molecule to which a second nucleic acid has been linked, and includes for example plasmids, cosmids or phages (as discussed in grater detail below). In certain embodiments of the present invention, the bioactive substance is the second nucleic acid. One type of transfer vector is an episome, i.e., a nucleic acid capable of extra-chromosomal replication.

In certain embodiments, a transfer vector may be an "expression vector," which refers to a replicable DNA construct used to express DNA which encodes the desired protein and which includes a transcriptional unit comprising an assembly of (i) genetic element(s) having a regulatory role in gene expression, for example, promoters, operators, or enhancers, operatively linked to (ii) a DNA sequence encoding a desired protein which is transcribed into mRNA and translated into protein, and (iii) appropriate transcriptional and translation initiation and termination sequences. In certain embodiments, the bioactive substance is the DNA sequence. The choice of promoter and other regulatory elements generally varies according to the intended host cell. In general, expression vectors of utility in recombinant DNA techniques are often in the form of "plasmids," which refer to circular double stranded DNA loops, which, in their vector form are not bound to the chromosome. The invention is intended to include such other forms of expression vectors which serve equivalent functions and which become known in the art subsequently hereto.

Certain transfer vectors contain regulatory elements for controlling transcription or translation, which may be generally derived from mammalian, microbial, viral or insect genes. The ability to replicate in a host, usually conferred by an origin of replication, and a selection gene to facilitate recognition of transformants, may additionally be incorporated.

Transfer vectors derived from viruses, which may be referred to as "viral vectors," may be employed in certain embodiments of the present invention. Some examples include retroviruses, adenoviruses and the like. Viral vectors are their uses in the present invention are discussed in more detail below. As for expression vectors, viral vectors may include regulatory elements.

The design of any transfer vector may depend on such factors as the choice of the host cell to be transformed and/or the type of protein desired to be expressed. Moreover, the vector's copy number, the ability to control that copy number and the expression of any other proteins encoded by the vector, such as antibiotic markers (e.g., ampicillin), may also be considered.

Some examples of expression vectors that may be used in certain embodiments of the present invention include the following. Suitable vectors for expression of a polypeptides include plasmids of the types: pBR322-derived plasmids, pEMBL-derived plasmids, pEX-derived plasmids, pBTac-derived plasmids and pUC-derived plasmids for expression in prokaryotic cells, such as E. coli. In some instances, it may be desirable to express the a protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

"Transgenic animal" is any animal, often a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The term "treating" as used herein is intended to encompass curing is well as ameliorating at least one symptom of any condition or disease.

2. General Introduction

The present invention contemplates encapsulating bioactive substances in coacervates. In certain embodiments, the coacervates are in the form of microspheres. A variety of different bioactive substances may be incorporated in such coacervates. In certain embodiments, the bioactive substance is a nucleic acid, such as a transgene. The nucleic acid may be contained in a transfer vector, which may include regulatory elements. A variety of different uses for the subject coacervates are contemplated by the present invention. Processes for preparing coacervates of the present invention are disclosed herein.

For those embodiments for which the therapeutic effect of the bioactive substance may be enhanced by intracellular delivery, such as a transgene, gene construct, expression vector or the like, a delivery agent to facilitate such delivery may also be encapsulated in the coacervate. When the bioactive substance is plasmid DNA, a possible delivery agent includes polylysine, polyarginine, bisguanidine cholesterol and other amphiphilic molecules. When the bioactive substance is a nucleic acid sequence contained in a viral vector, the delivery agent is usually the virus particle corresponding to the virus in which the nucleic acid sequence is contained. The mechanisms by which these different delivery agents facilitate delivery of the bioactive substance varies.

By encapsulating the bioactive substance in a coacervate it is possible, in certain embodiments, to provide a steady dosage of such bioactive substance through a sustain release process. In addition, such encapsulation may protect the bioactive substance, delivery agent, or other materials from undesirable immunogenic, proteolytic or other events that would reduce the efficacy of the bioactive substance.

While not wishing to be bound by any particular theory, and without limiting any embodiment of the invention to a particular mechanism of action, control release of the majority of any encapsulated bioactive substance or other material from a coacervate occurs in all likelihood through biodegradation of the coacervate. In those embodiments of the present invention in which gelatin is a constituent of the coacervate, it is believed that proteases are responsible for biodegradation and concomitant release of bioactive substance or other material. Diffusion of any bioactive substance or other material from the coacervate is possible; however, such diffusion in all likelihood does not account for any significant portion or release observed in certain embodiments of the invention because the diffusion coefficient for such substance or other material is probably low. In addition, if any bioactive substance or other material is charged, such as a nucleic acid or a virus, which has charged moieties on its surface, then diffusion release from the coacervate is probably even less favored.

In addition to intracellular delivery of the bioactive substance mediated by a delivery agent after release from the subject microspheres, it also possible that microspheres of the present invention may undergo endocytosis, thereby obtaining access to the cell. The frequency of such an endocytosis process will likely depend on the size of any coacervate. Any biodegradation of a coacervate may increase the frequency of such endocytosis because the microspheres will presumably diminish in size.

3. Coacervates

Coacervation is a process of separation of colloidal solutions into two or more immiscible liquid phases. For example, when oppositely charged polyelectrolytes are brought to contact in aqueous medium, a spontaneous phase separation occurs with the result of formation of coacervates. The coacervates is a phase where colloids (e.g., polymers) are concentrated.

There are two general types of coacervates. In the first, "complex coacervates" are formed when hydrophilic materials are caused to emerge from solution by being complexed with another hydrophilic material which process decreases the collective solubilities of the materials in the solution. Thus, generally, the emergent phase includes the predominant portion of both hydrophilic materials.

In contrast, in "simple coacervates," a single kind of hydrophilic material is caused to emerge from solution by the addition of a phase-separation-inducing substance, such as a non-solvent, a micro-salt, or by a change in the temperature. The emergent phase then contains a relatively high concentration of the hydrophilic material and the phase-separation inducing substance is substantially evenly distributed between the emergent phase and the remaining continuous phase.

For both types of coacervates, usually not all of the starting materials will combine to form the desired coacervate. That is, the synthesis of any coacervate does not give a 100% yield from the starting materials. In general, only a portion of the molecules in solution will aggregate to form coacervates.

A. Constituents of Coacervates and Bioactive Substances and Other Materials Encapsulated Therein Components and constituents that may be used to form complex coacervates comprise anionic and cationic molecules, and such molecules may be naturally occurring or synthetic. By "cationic" or "anionic" molecule is meant a molecule which, under the conditions of coacervation, carries a net positive or negative charge, respectively. Many such molecules are amphoteric and contain both acidic and basic groups. Under prevailing pH conditions, these molecules may be either cationic or anionic. Representative cationic molecules include: albumin; collagen; elastin; gelatin; globulins; alginate; polymers containing quaternary salt groups, including heterocyclic quaternary salt groups such as quaternized pyridinyl groups, e.g. those found in quaternized poly(vinylpyridine) polymers, as well as polymers including aliphatic quaternary salt groups; and polymers containing ammonium salt groups such as poly(dimethyl-diallyl-ammonium chloride) among others, derivatives thereof and mixtures thereof.

Representative anionic molecules include: chondroitin sulfate, dermatan sulfate, heparin, polylysine, polyornithine, heparan sulfate, hyaluronic acid, keratan sulfate, arabic acid, cellulose sulfate, carboxymethylcellulose, carrageenans, polyacrylic acid, polyoxyethylene crosslinked polyacrylic acid, polyphosphazine, glycolic acid esters of polyphosphazine, lactic acid esters of polyphosphazine, hyaluronic acid, polygalacturonic acid, polyglucuronic acid, polyphenylene sulfonic acid, and polyvinylcarboxylic acid, among others, derivatives thereof and mixtures thereof. The choice of cationic and anionic molecules depends on a number of factors, including for example the intended use of the resultant coacervates, the amounts of the different constituents, and the nature of the bioactive substance.

The choice of the cationic and anionic molecules may depend on the final or intended use of the present compositions, and they are expected to possess a high degree of biocompatibility. In certain embodiments, gelatin is used as the cationic molecule in the present invention, and an alginate compound is used as the anionic molecule. Aginate is a hydrophilic colloid which is found in seaweed, and it typically exists as a salt associated with a positively charged counterion, such as sodium, potassium or calcium. Gelatin is a protein or mixture of proteins obtained by hydrolysis of collagen.

If the bioactive substance is a charged molecule at the pH at which coacervate formation takes place, the molecule may participate in the complex coacervation process to form the coacervate wherein the substance is entangled in and with the coacervate matrix. For example, any charged delivery agent, such as a cationic amphiphile, may take part in the coacervation formation. In certain embodiments, the bioactive substance to be encapsulated in the coacervate may serve as either one of the cationic or anionic constituents of the coacervate. U.S. Pat. No. 5,834,271 describes using an enzyme as the anionic constituent of a coacervate.

The constituents of any coacervate may be modified before preparation of the coacervate composition to alter, for example, certain properties of the resulting coacervate. In certain instances, the modification is a chemical one that alters the pKa of the of the functional groups of the constituent.

In another aspect of the present invention, the coacervates may be crosslinked. Such crosslinks may be between the same or different constituents of any coacervate, and may involve bioactive substances or other materials incorporated therein. There are a number of agents and methods of using the foregoing, that may be used to effect such crosslinking. In one embodiment, crosslinking may be effected by use of a gelatin-hardening agent such as glutaraldehyde. In other embodiments, epichlorohydrin or acrolein may be used as the crosslinking agent.

In another embodiment, crosslinking may be obtained by including in a coacervate a constituent or other material that is photopolymerizable. Some examples are presented in U.S. Pat. No. 5,858,746. In addition, any photopolymerizable component of a coacervate may be used as a primer or coupling agent to modify the exterior of the coacervate. For example, such primer or coupling agent may be used to react to photopolymerizable PEG to enhance biocompatibility and to increase adhesion to cells, cell aggregates, tissues and synthetic materials.

In still other embodiments, calcium or other multivalent counterions may be used as crosslinking agents to crosslink coacervates of the present example. Calcium salts, such as calcium chloride, are used in certain embodiments. In one example, coacervation of gelatin and alginate in the presence of recombinant *adenovirus* yields spheres containing the virus. The formed microspheres may be stabilized by adding calcium ions to the mixture.

Bioactive substances and other materials may be loaded into coacervates of the present invention during their preparation. The amount of bioactive substance desirable in coacervates of the present invention will depend on a number of factors, including: (i) the identity of the bioactive substance; (ii) the coacervate's intended use, including any desired therapeutic effect for in vivo use; (iii) the chemical and physical properties of the coacervate, including the release rate of encapsulated bioactive substance or other material under different conditions. The concentration bioactive substance and other material typically does not exceed 50 weight %.

In certain embodiments, the present invention contemplates incorporating sufficient bioactive substance to produce a therapeutically beneficial result. In those embodiments in which the bioactive substance is a nucleic acid contained in a virus, the amount of virus or virus particle loaded in any coacervate may range from less than about 0.05 to more than about 30 weight percent, or 0.1, 0.25, 0.5, 0.75, 1.0, 1.5, 2.0, 3.0, 4.0, 5.0, 6.0, 7.0, 8.0, 9.0, 10, 15, 20 and 25. For example, a virus particle loaded at a 2% level means that there are 2 mg of such virus or particle per 100 mg of coacervate.

In addition to bioactive substances, other materials, including for example delivery reagents, may be incorporated into a coacervate. Such additional materials may affect the therapeutic and other characteristics of the coacervate that results. One example of such another material is an adjuvant. (Such materials may also be termed bioactive substances if appropriate.)

The amount of delivery agent to be encapsulated in coacervates of the present invention will depend on a number of factors, most notably the method by which the delivery agent facilitates intracellular delivery of any bioactive substance. For example, if the bioactive substance is a lipid and the bioactive substance is a expression vector, then the to amount of lipid should be calibrated to the amount of bioactive substance so as to optimize intracellular delivery. In certain embodiments, in which the bioactive substance is a nucleic acid and the delivery agent is a virus containing the nucleic acid sequence, then the ratio of amount of delivery agent, i.e., virus or virus particle, to bioactive substance, nucleic acid sequence, will usually be fixed.

Another example of such materials are fillers, such as bovine serum albumin (BSA) or mouse serum albumin (MSA). In certain embodiments, when incorporated in combination with the bioactive substance, the amount of filler may range from about 1 to about 100 times or more the amount of bioactive substance, by weight, or a ratio of about 2.5, 5, 10, 25, 50, 75 weight filler to bioactive substance. For example, if the bioactive substance is a nucleic acid, if 1 mg of nucleic acid is loaded into 100 mg of coacervate, the filler may represent about 1 mg to about 100 mg in weight. As expressed in terms of percent loading, for a nucleic acid load level of 0.1%, a filler would amount to about 0.1% to 10% or more.

Incorporation of such fillers may affect the release rate of bioactive substance or other material incorporated into subject coacervates. Other fillers known to those of skill in the art, such as carbohydrates, sugars, saccharides, and polysaccharides, including for example mannitose and sucrose, may be used in certain embodiments in the present invention.

Alternatively, materials that augment the therapeutic effect of the bioactive substance may be incorporated into the coacervate. (Such materials may also be referred to as bioactive substances as appropriate.) For example, an encapsulated bioactive substance may be an expression vector that encodes a antigen. Co-encapsulation of one or more cytokines, such as IFN-γ and IL-4, may affect the immunogenic response afforded any such nucleic acid. The amount of any such augmenting agent to be loaded into any coacervate will depend on a variety of factors, including the nature of the such agent, the coacervate, whether there are any other materials incorporated in addition to the bioactive substance, and the like. For any such agent, the present invention contemplates incorporating a sufficient amount to augment the therapeutic effect of the bioactive substance. In other embodiments, the amount of such augmenting agent may range from about 0.005% up to about 25%, or alternatively 0.01, 0.05, 0.1, 0.25, 0.5, 1.0, 2.5, 5.0, 10, 15 or 20%.

In another aspect, the present invention contemplates loading more than two different materials into any coacervate. In certain embodiments, three, four, five or more bioactive substances, delivery agents, augmenting agents, fillers or other materials may be incorporated in any coacervate.

In another aspect, coacervates of the present invention may contain particles useful to locate the coacervate for diagnostic applications and the like. In certain embodiments, coacervates according to the present invention may contain paramagnetic, superparamagnetic or ferromagnetic substances which are of use in magnetic resonance imaging (MRI) diagnostics. For example, submicron particles of iron or a magnetic iron oxide may be incorporated into coacervates to provide ferromagnetic or superparamagnetic particles. Paramagnetic MRI contrast agents principally comprise paramagnetic metal ions, such as gadolinium ions, held by a chelating agent which prevents their release (and thus substantially reduces their toxicity). In another embodiment, coacervates of the present invention may contain submicron particles, such as magnetic iron oxide, which permit the magnetic separation of coacervates. Other labeled compounds, such as radionucleides, e.g., $^3$H, $^{14}$C, $^{18}$F, $^{32}$P, $^{99m}$Tc, and $^{125}$I, may also be utilized for visualizing cells and tissues, to which coacervates may be bound, by means of X-rays or magnetic resonance imaging. Coacervates of the present invention may also contain in certain embodiments ultrasound contrast agents such as heavy materials, e.g. barium sulphate or iodinated compounds, to provide ultrasound contrast media.

In another aspect of the invention, coacervates of the present invention may be conjugated to targeting molecules attached to the surface of the coacervate, such as monoclonal antibodies that preferentially bind to a receptor or other site of interest, e.g., to the lung or hematopoietic system. In certain embodiments, such targeting may achieve targeted gene delivery in vivo. To attach targeting molecules to the surface of any coacervate, it may be necessary to encapsulate in coacervates linker molecules. Such linker molecules may be used to attach targeting molecules. Alternatively, the constituents that form the coacervate may contain functional groups that allow for attachment of targeting molecules.

B. Preparation and Formation of Coacervates

Coacervate formation for encapsulating or incorporating a bioactive substance or other material may be achieved by controlling the phase separation conditions such as the choice and concentrations of suitable polyelectrolytes, pH and temperature.

Typically, in preparing the coacervates of the present invention, both types of components are brought into contact in a medium under predetermined mixing conditions. In certain embodiments, the medium is substantially, if not entirely, aqueous. The concentration of the two molecules in aqueous solution before mixing will depend on the identity of the two molecules and the coacervate desired. Generally, the concentration will not exceed 15% (w/vol). In certain embodiments, the mixing may be carried out using equivolumes of the two solutions of the anionic and cationic molecules that constitute the coacervate.

In one embodiment, an aqueous gelatin solution and an aqueous chondroitin sulfate solution are mixed to form a coacervate. Gelatin may be present in the aqueous solution in a concentration of from about 0.1% to about 10% (w/vol), and chondroitin sulfate may be present in the aqueous solution in a concentration of from about 0.05% to about 5% (w/vol). Outside these concentration ranges, the formation of this particular coacervate appears to be adversely effected.

Temperature may affect the formation of coacervates. The temperature to be employed in forming coacervates may vary somewhat with the particular method employed. In certain embodiments, a temperature from ambient temperature to about 50° C. may be used. Particular temperatures include 15, 20, 30, 40 and 50° C. The size of any microspheres formed in the preparation of coacervates may be susceptible to the temperature at which the coacervate is formed. For instance, in a coacervate prepared from gelatin, the higher the temperature of the gelatin solution, the smaller the microspheres of the coacervate usually formed.

The pH to be employed in forming coacervates may vary over a fairly wide range. The yield and size of coacervate compositions attained may be influenced by the pH. In certain embodiments, in which gelatin is a constituent, a pH of from about 3.5 to about 6.5 is used to form the coacervate (the latter of which corresponds to the isoelectric point of gelatin). In one embodiment, a desirable size and yield of coacervates is obtained at a pH of about 5.0.

Usually, the bioactive substances or other materials may be added to either solution of constituent molecules. For example, the recombinant virus in the exemplification below may be added either to the gelatin solution or to the alginate solution prior to the formation of coacervates. If the active substance is water-soluble, a solution generally results; whereas, if the active substance is water-insoluble, an emulsion or suspension generally results.

Upon mixing of the solutions containing the constituents of the coacervate, e.g., the cationic and anionic molecules, coacervation takes place in the reaction medium to form coacervates. In certain embodiments, such coacervates are microspheres.

Usually subsequent to coacervate formation, crosslinking of the coacervates may be completed if desired as described above.

The coacervates re usually recovered from the reaction medium by a conventional means, e.g., decantation, filtration or centrifugation. The coacervates may be washed and dried in a standard technique, e.g., lyophilization. In certain embodiments, in which the bioactive substance and delivery agent are a viral vector, lyophilization of microspheres greatly minimized bioactivity loss. Consequently, for such embodiments, it is possible to store microspheres of the present invention at 4° C. Such microspheres may be ideally suited for inclusion in kits of the present invention.

After preparation of coacervates, the present invention contemplates additional processing or manufacturing steps that do not destroy or otherwise impair the integrity of such coacervates. For example, suspending any coacervate in solution does materially impair such coacervate. Alternatively, coacervates of the present invention may be formulated in a pharmaceutical composition for administration to a patient. Alternatively, derivatizing or otherwise modifying the exterior of any coacervate, by physical, chemical or other means, does not impair such coacervate, as long as any encapsulated bioactive substance or other material encapsulated in such coacervate may still be released in a controlled fashion, albeit at a different location in vivo, release rate or profile.

C. Properties of Coacervates of the Present Invention

In certain embodiments, formation of coacervates generates, in a reproducible manner, microspheres with a relatively narrow size distribution. In such embodiments, microspheres generally do not contain significant amount of larger size aggregates or amorphous precipitate.

In certain embodiments, the coacervates of the present invention, upon contact with body fluids or other liquids, may release bioactive substance or other material encapsulated therein. The release rate of any bioactive substance or other material from coacervates of the present invention may be optimized by adjusting the formulation and preparation of the coacervates. Relevant variables include the identity of the constituents of the coacervate, the ratio of such constituents to one another, the identity of any bioactive substance or other material encapsulated in the coacervate, the degree of crosslinking, the method of preparation of the coacervate, and the like.

The release rate will vary with different embodiments of the present invention. For example, one subject formulation may require at least an hour to release a major portion of the active substance into the surrounding medium, whereas another formulation may require about 1–24 hours, or even much longer. In certain embodiments, such release may result in release (over, say 1 to about 2,000 hours, or alternatively about 2 to about 800 hours) of the bioactive substance or other material encapsulated in the coacervate. In certain embodiments, such substance or other material may be released in an amount sufficient to produce a therapeutically beneficial response.

The release profile of any bioactive substance or other material from a coacervate of the present invention may vary in different embodiments. In one embodiment of the present invention, the bioactive substance or other material is released from coacervate in a pulsatile manner. For example, such a pulsatile manner may involve release of the bioactive substance or other material in three phases: an initial burst, a slow release, and a second burst. In another embodiment of the present invention, the bioactive substance or other material is released in a sustained manner. In still other embodiments, a significant portion of the bioactive substance or other material is released in an initial phase. In still other embodiments, the release profile is bi-phasic.

The release of any bioactive substance or other material herein may be determined using in vitro assays. One such assay is described in the exemplification below. Another assay that is known in the art involves degradation of any subject coacervate in a 0.1 M PBS solution (pH 7.4) at 37° C. For purposes of the present invention, the term "PBS protocol" is used herein to refer to such protocol.

In certain instances, the release rates of the different embodiments of the present invention may be compared by subjecting them to the same assay. In certain instances, it may be necessary to process the coacervates in the same fashion to allow direct and relatively accurate comparisons of different embodiments to be made. Such comparisons may indicate that any one embodiment releases incorporated bioactive substance or other material at a rate from about 2 or less to about 1000 or more times faster than another embodiment. Alternatively, a comparison may reveal a rate difference of about 3, 5, 7, 10, 25, 50, 100, 250, 500 or 750. Even higher rate differences are contemplated by the present invention.

The release rate of any bioactive substance or other material may also be characterized by the amount of such substance or other material released per day per mg of coacervate. For example, in certain embodiments, the release rate may vary from about 1 ng or less of any such substance or other material per day per mg of coacervate to about 5000 or more ng/day.mg. Alternatively, the release rate may be about 10, 25, 50, 75, 100, 125, 150, 175, 200, 250, 300, 350, 400, 450, 500, 600, 700, 800 or 900 ng/day.mg. In still other embodiments, the release rate of any incorporated material may be 10,000 ng/day.mg or even higher.

In those embodiments of the present invention in which a virus is encapsulated in the subject coacervates, so that the bioactive substance is a nucleic acid of interest contained in a viral vector and a delivery agent is the virus particle, the release rate may also be quantified by "PFU," or plaque forming units. In such embodiments, PFUs designate the number of infectious virions. This unit only quantifies those viruses or virus particles that are bioactive, whereas the mass measurement described above counts both bioactive and non-bioactive viruses or viral particles. In certain embodiments, the range of PFUs that any subject coacervate may release over any particular time period may range from less than about 100 PFUs to more than about $10^9$ PFUs.

In another aspect, the rate of release of any bioactive substance or other material from any coacervate of the present invention may be presented as the half-life of such substance or other material in such coacervate.

In addition to the embodiment involving protocols for in vitro determination of release rates, in vivo protocols, whereby release rates for different coacervates may be determined in vivo, are also contemplated by the present invention. One such assay is presented in the exemplification below. Comparisons of release rates for different embodiments of the subject coacervates may be made for in vivo assays in a similar manner as for in vitro assays. Other assays useful for determining the release of any coacervate of the present invention are known in the art.

4. Delivery Agents

In accordance with the subject invention, bioactive substances, including nucleic acids, transgenes, and the like, may be coencapsulated in a coacervate with any appropriate delivery agent. Approaches contemplated by the present invention include insertion of any gene or other nucleic acid of interest in viral vectors including recombinant retroviruses, adenovirus, adeno-associated virus, and herpes simplex virus-1, or recombinant bacterial or eukaryotic plasmids. Viral vectors may be used to transfect cells directly, with the virus or virus particle serving as a delivery agent; plasmid DNA or other nucleic acid may be delivered with the help of, for example, the following delivery agents: cationic liposomes (lipofectin), polylysine conjugates, polyarginine, bisguanidine cholesterol, artificial viral envelopes and other like intracellular carriers, etc. It will be appreciated that because transduction of appropriate target cells represents the critical first step in gene therapy, choice of the particular delivery agent will depend on such factors as the phenotype of the intended host and the route of administration, e.g. locally or systemically.

One approach for in vivo introduction of gene construct, expression vector, or other nucleic acid of interest into a cell is by use of a viral vector containing nucleic acid, e.g. a cDNA, encoding the gene product. Infection of cells with a viral vector has the advantage that a large proportion of the targeted cells may receive the nucleic acid. Additionally, molecules encoded within the viral vector, e.g., by a cDNA contained in the viral vector, are expressed efficiently in cells which have taken up viral vector nucleic acid.

In certain embodiments, the delivery agent for any viral vector is the virus or virus particle corresponding to the viral vector. Generally, such virus or virus particle envelops or encapsulate its corresponding viral vector, although the present invention contemplates that in any mixture of viral vectors, not all viral vectors will not be so enveloped or encapsulated. In most instances, substantially all viral vectors in such a mixture would be so enveloped or encapsulated.

Retrovirus vectors and adeno-associated virus vectors are one recombinant gene delivery system able to transfer of exogenous genes in vivo, particularly into humans. These vectors provide efficient delivery of genes into cells, and the transferred nucleic acids are stably integrated into the chromosomal DNA of the host. A prerequisite for the use of retroviruses ensure the safety of their use, particularly with regard to the possibility of the spread of wild-type virus in the cell population. The development of specialized cell lines (termed "packaging cells"), which produce only replication-defective retroviruses, has increased the utility of retroviruses for gene therapy. Such defective retroviruses are well characterized for use in gene transfer for gene therapy purposes (for a review see Miller, *Blood* 76:271 (1990)). Thus, recombinant retrovirus may be constructed in which part of the retroviral coding sequence (gag, pol, env) has been replaced by a gene or other nucleic acid of interest, rendering the retrovirus replication defective. The replication defective retrovirus is then packaged into virions which may be used to infect a target cell through the use of a helper virus by standard techniques. Protocols for producing recombinant retroviruses and for infecting cells in vitro or in vivo with such viruses may be found in *Current Protocols in Molecular Biology*, Ausubel et al. (eds.) Greene Publishing Associates, (1989), Sections 9.10–9.14 and other standard laboratory manuals. Examples of suitable retroviruses include pLJ, pZIP, pWE and pEM, which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. *Science* 230:1395–1398 (1985); Danos and Mulligan *Proc. Natl. Acad. Sci. USA* 85:6460–6464 (1988); Wilson et al., *Proc. Natl. Acad. Sci. USA* 85:3014–3018 (1988); Armentano et al., *Proc. Natl. Acad. Sci. USA* 87:6141–6145 (1990); Huber et al., *Proc. Natl. Acad. Sci. USA* 88:8039–8043 (1991); Ferry et al., *Proc. Natl. Acad. Sci. USA* 88:8377–8381 (1991); Chowdhury et al., *Science* 254:1802–1805 (1991); van Beusechem et al., *Proc. Natl. Acad. Sci. USA* 89:7640–7644 (1992); Kay et al., *Human Gene Therapy* 3:641–647 (1992); Dai et al., *Proc. Natl. Acad. Sci. USA* 89:10892–10895 (1992); Hwu et al., *J. Immunol.* 150:4104–4115 (1993); U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject coacervates, it is important to note that a prerequisite for the successful infection of target cells by most retroviruses, and therefore for stable introduction of the recombinant gene, is that the target cells must be dividing. In general, this requirement will not be a hindrance to use of retroviral vectors to deliver a subject gene or other nucleic acid. In fact, such a limitation on infection may be beneficial in circumstances in which the tissue (e.g., nontransformed cells) surrounding the target cells does not undergo extensive cell division and is therefore refractory to infection with retroviral vectors.

Furthermore, it has been shown that it is possible to limit the infection spectrum of retroviruses, and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., *PNAS* 86:9079–9083 (1989); Julan et al. *J. Gen Virol* 73:3251–3255. (1992); and Goud et al., *Virology* 163:251–254 (1983)); or coupling cell surface ligands to the viral env proteins (Neda et al., *J Biol Chem* 266:14143–14146 (1991)). Coupling may be in the form of the chemical cross-linking with a protein or other variety (e.g. lactose to convert the env protein to an asialoglycoprotein), as well as by generating fusion proteins (e.g. single-chain antibody/env fusion proteins). This technique may be used to limit or otherwise direct the infection to certain tissue types, and may also be used to convert an ecotropic vector into an amphotropic vector. Moreover, use of retroviral gene delivery may be further enhanced by the use of tissue or cell-specific regulatory elements which control expression of the gene of the retroviral vector.

Another viral gene delivery system useful in the present invention utilizes adenovirus-derived vectors. The genome of an adenovirus may be manipulated such that it encodes a gene product of interest, but is inactivate in terms of its ability to replicate in a normal lytic viral life cycle (see, for example, Berkner et al., *BioTechniques* 6:616 (1988); Rosenfeld et al., *Science* 252:431–434 (1991); and Rosenfeld et al., *Cell* 68:143–155 (1992)). Suitable adenoviral vectors derived from the adenovirus strain Ad type 5 d1324 or other strains of adenovirus (e.g., Ad2, Ad3, Ad7) are well known to those skilled in the art. Recombinant adenoviruses may be advantageous in certain circumstances in that they are not capable of infecting nondividing cells and can be used to infect a wide variety of cell types, including endothelial cells (Lemarchand et al., *Proc. Natl. Acad. Sci. USA* 89:6482–6486 (1992)), and smooth muscle cells (Quantin et al., *Proc. Natl. Acad. Sci. USA* 89:2581–2584 (1992)). Furthermore, the virus particle is relatively stable and amendable to purification and concentration, and as above, may be modified so as to affect the spectrum of infectivity. Additionally, introduced adenoviral DNA (and foreign DNA contained therein) is not integrated into the genome of a host cell but remains episomal, thereby avoiding potential problems that may occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, *J. Virol.* 57:267 (1986)). Most replication-defective adenoviral vectors currently in use and therefore favored by the present invention delete almost all of the viral E1 and E3 genes but otherwise retain as much as 80% of the adenoviral genetic material (see, e.g., Jones et al., *Cell* 16:683 (1979); Berkner et al., supra; and Graham et al. in *Methods in Molecular Biology* 7:109–127 (1991)). Expression of the inserted gene or other nucleic acid may be under control of, for example, the E1A promoter, the major late promoter (MLP) and associated leader sequences, the E3 promoter, or exogenously added promoter sequences.

Yet another viral vector system useful for delivery of a nucleic acid of interest is the adeno-associated virus (AAV). Adeno-associated virus is a naturally occurring defective virus that requires another virus, such as an *adenovirus* or a herpes virus, as a helper virus for efficient replication and a productive life cycle. (For a review see Muzyezka et al. *Curr. Topics in Micro. and Immunol.* 158:97–129 (1992)). It is also one of the few viruses that may integrate its DNA into non-dividing cells, and exhibits a high frequency of stable integration (see for example Flotte et al., *Am. J. Respir. Cell. Mol. Biol.* 7:349–356 (1992); Samulski et al., *J. Virol.* 63:3822–3828 (1989); and McLaughlin et at., *J. Virol.* 62:1963–1973 (1989)). Vectors containing as little as 300 base pairs of AAV may be packaged and may integrate. Space for exogenous DNA is limited to about 4.5 kb. An AAV vector such as that described in Tratschin et al., *Mol. Cell. Biol.* 5:3251–3260 (1985) may be used to introduce DNA into cells. A variety of nucleic acids have been introduced into different cell types using AAV vectors (see for example Hermonat et al., *Proc. Natl. Acad. Sci. USA* 81:6466–6470 (1984); Tratschin et al., *Mol. Cell. Biol.* 4:2072–2081 (1985); Wondisford et al., *Mol. Endocrinol.* 2:32–39 (1988); Tratschin et al., *J. Virol.* 51:611–619 (1984); and Flotte et al., *J. Biol. Chem.* 268:3781–3790 (1993)).

Other viral systems that may have application in gene delivery systems of the present invention have been derived from herpes virus, vaccinia virus, and several RNA viruses. In particular, herpes virus vectors may provide a unique strategy for persistent expression of the a nucleic acid of interest in cells of the central nervous system and ocular tissue (Pepose et al., *Invest Ophthalmol Vis Sci* 35:2662–2666 (1994)).

In addition to viral transfer methods, such as those illustrated above, other types of delivery agents, and methods for their use, are contemplated by the present invention. In certain instances, such non-viral agents and methods may be employed to cause expression of subject recombinant proteins in the tissue of a host. Most nonviral methods of gene transfer rely on normal mechanisms used by mammalian cells for the uptake and intracellular transport of macromolecules. In certain embodiments, non-viral gene delivery systems of the present invention rely on endocytic pathways for the uptake of the gene by the targeted cell. Exemplary gene delivery systems of this type include liposomal derived systems, poly-lysine conjugates, artificial viral envelopes, amphiphilic molecules, and other materials designed to facilitate entry of any nucleic acid into a cell.

In a representative embodiment, a gene encoding one of the subject proteins may be entrapped in liposomes bearing positive charges on their surface (e.g., lipofectins). For example, lipofection of neuroglioma cells may be carried out using liposomes tagged with monoclonal antibodies against glioma-associated antigen (Mizuno et al., *Neurol. Med. Chir.* 32:873–876 (1992)).

A variety of amphiphilic compounds may serve as delivery agents. See generally U.S. Pat. No. 5,925,628. Compounds that have both a polar and non-polar domain may be termed amphiphiles, and many lipids and synthetic lipids that have been used as delivery agents meet this definition. One particularly important class of such amphiphiles is the cationic amphiphiles. In general, cationic amphiphiles have polar groups that are capable of being positively charged at or around physiological pH, and this property may be important in determining how amphiphiles interact with bioactive substances. Two examples of such amphiphiles include bis-guanidinium-spermidine-cholesterol and bis-guanidinium-spermidine-trencholesterol derivatives. See, e.g., Vigneron et al., *Proc. Natl. Acad. Sci. USA* 93:9682–86 (1996). Other well-known amphiphilic compounds include: DOTMA (Felgner et al. *Proc. Natl. Acad. Sci. USA* 84:7413–17 (1987)); and DOGS (Behr et al. *Proc. Natl. Acad.*

Sci. USA 86:6982–86 (1989)). See also Felgner et al. *Methods in Enzymology* 5:67–75 (1993); and U.S. Pat. Nos. 5,283,185, 5,264,618 and 5,334,761.

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject gene construct may be used to transfect cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject genes or other nucleic acids via receptor-mediator endocytosis may be improved using agents which enhance escape of the gene from the endosomal structures. For instance, whole adenovirus or fusogenic peptides of the influenza HA gene product may be used as part of the delivery system to induce efficient disruption of DNA-containing endosomes (Mulligan et al., *Science* 260–926 (1993); Wagner et al., *PNAS* 89:7934 (1992); and Christiano et al., *PNAS* 90:2122 (1993)).

5. Administration of Coacervates of the Present Invention

Coacervates of the present invention may be administered by various means, depending on their intended use, as is well known in the art. For example, if coacervates are to be administered orally, they may be formulated as tablets, capsules, granules, powders or syrups. Alternatively, formulations of the present invention may be administered parenterally as injections (intravenous, intramuscular or subcutaneous), drop infusion preparations, or suppositories. For application by the ophthalmic mucous membrane route, coacervates may be formulated as eye drops or eye ointments. These formulations may be prepared by conventional means, and, if desired, coacervates may be mixed with any conventional additive, such as an excipient, a binder, a lubricant, a corrigent, a solubilizing agent, a suspension aid, an emulsifying agent or coating agent and the like.

Certain formulations, methods of formulation and modes of administration may not be amenable with all the subject coacervates. For example, coacervates of the subject invention, depending on the nature of the coacervate and degree of crosslinking, may be somewhat sensitive to mechanical action. Likewise, certain subject coacervates may be sensitive to particular chemical treatments, excipients or carriers. It may be necessary to determine empirically to which formulations, formulating methods and modes of administration different coacervates of the present invention may be subjected without significant loss of bioactivity.

In particular embodiments, the gene delivery systems may be introduced into a patient by any of a number of methods, each of which is familiar in the art. For instance, a pharmaceutical preparation of the gene delivery system may be introduced systemically, e.g. by intravenous injection, and specific transduction of the target cells occurs predominantly from specificity of transfection provided by the gene delivery vehicle, cell-type or tissue-type expression due to the regulatory elements controlling expression of the gene. In other embodiments, initial delivery of the recombinant gene is more limited with introduction into the animal being quite localized. For example, the gene delivery vehicle may be introduced by catheter (see U.S. Pat. No. 5,328,470) or by stereotactic injection (e.g. Chen et al., *PNAS* 91: 3054–3057 (1994)).

In the event that any coacervate of the present invention is lyophilized after preparation, it may be desirable, depending on the pharmaceutical formulation intended, to rehydrate the coacervates before formulating them.

In formulations of the subject invention, wetting agents, emulsifiers and lubricants, is such as sodium lauryl sulfate and magnesium stearate, as well as coloring agents, release agents, coating agents, sweetening, flavoring and perfuming agents, preservatives and antioxidants may be present in the subject compositions.

Formulations that may be useful in the methods and compositions of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of coacervates which may be combined with a carrier material to produce a single dose vary in part on the subject being treated, and the particular mode of administration.

Methods of preparing these formulations or compositions include the step of bringing into association coacervates with the carrier and, optionally, one or more accessory ingredients. In general, the formulations are prepared by uniformly and intimately bringing into association coacervates thereof with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of coacervate thereof as an active ingredient. Coacervates may also be administered as a bolus.

In solid dosage forms for oral administration (capsules, tablets, pills, dragees, powders, granules and the like), the coacervate is mixed with one or more pharmaceutically-acceptable carriers. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the coacervates thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the coacervate, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the coacervates thereof, may contain suspending agents as, for example, ethoxylated isostearyl alcohols, polyoxyethylene sorbitol and sorbitan esters, microcrystalline cellulose, aluminum metahydroxide, bentonite, agar—agar and tragacanth, and mixtures thereof.

Formulations for rectal or vaginal administration may be presented as a suppository, which may be prepared by mixing coacervates with one or more suitable non-irritating excipients or carriers comprising, for example, cocoa butter, polyethylene glycol, a suppository wax or a salicylate. Such excipients or carriers are generally solid at room temperature, but liquid at body temperature, and therefore, they will melt in the rectum or vaginal cavity and release coacervates.

Dosage forms for transdermal administration of a coacervate includes powders, sprays, ointments, pastes, creams, lotions, gels, solutions, patches and inhalants. File coacervates may be mixed under sterile conditions with a pharmaceutically-acceptable carrier, and with any preservatives, buffers, or propellants which may be required.

Coacervates may alternatively be administered by aerosol. Such administration may be accomplished by preparing an aqueous aerosol, liposomal preparation or solid particles containing the coacervates. A non-aqueous (e.g., fluorocarbon propellant) suspension may be used. Sonic nebulizers may be used because they minimize exposing the agent to shear, is which may result in degradation of the coacervate.

Ordinarily, an aqueous aerosol is made by formulating an aqueous solution or suspension of coacervates together with conventional pharmaceutically acceptable carriers and stabilizers. The carriers and stabilizers vary with the requirements of the particular coacervate, but typically include non-ionic surfactants (Tweens), Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise coacervates in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetables oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

6. Exemplary Uses of Coacervates of the Present Invention

A. Genes and Other Nucleic Acids

A variety of genes and other nucleic acids may be incorporated into the subject coacervates for use in in vitro and in vivo transfection systems. These recombinant sequences may be transcribable to RNA and/or expressible is protein molecules which render them useful as therapeutic agents.

Proteins of use in gene therapy include various hormones, growth factors, enzymes, lymphokines, cytokines, receptors, and the like. For example, the vectors of the present invention may be used for direct gene replacement therapy, as in the case of replacing the is function of a non-functional gene. Such direct replacement therapies have useful veterinary applications as well.

Among the genes that may be transferred in accordance with the invention are those encoding polypeptides that are absent, are produced in diminished quantities, or are produced in mutant form in individuals suffering from a genetic disease. Other genes of interest are those that encode proteins that have been engineered to circumvent a metabolic defect or proteins that, when expressed by a cell, may adapt the cell to grow under conditions where the unmodified cell would be unable to survive, or would become infected by a pathogen.

In addition the vectors may be used to produce anti-sense nucleic acids in target cells. Antisense therapy involves the production of nucleic acids that bind to a target nucleic acid, typically an RNA molecule, located within cells. The term antisense is so given because the oligonucleotides are typically complementary to mRNA molecules ("sense strands") which encode a cellular product targeted to selected cellular or viral gene expression products. Exemplary modes by which sequences may be targeted for therapeutic applications include: blocking the interaction of a protein with an RNA sequence (e.g., the interaction of RNA virus regulatory proteins with their RNA genomes); and targeting sequences causing inappropriate expression of cellular genes.

In addition, the vectors of the present invention may be used to deliver sequences encoding catalytic RNA molecules into cells. For example, DNA sequences encoding a ribozyme of interest may be cloned into a vector of the present invention. Such a ribozyme may be a hammerhead ribozyme capable of cleaving a viral substrate, such as the Human Immunodeficiency Virus genome or an undesirable messenger RNA, such as that of an oncogene. The DNA-encoding ribozyme sequences may be expressed in tandem with tRNA sequences, with transcription directed from, for example, mammalian tRNA promoters.

In another embodiment, the coacervates may be used to deliver a nucleic acid which is itself a "decoy," or which is transcribable by the host cell to provide a decoy nucleic acid. A decoy nucleic acid is a nucleic acid having a sequence recognized by a regulatory nucleic acid binding protein (i.e., a transcription factor). Upon expression, the transcription factor binds to the decoy nucleic acid, rather than to its natural target in the genome. Useful decoy nucleic acid sequences include any sequence to which a transcription factor binds.

In still other embodiments, the subject coacervates may be used to transfect a cell with a recombinant gene encoding a "transdominant" protein. Such proteins may be dominant positive (agonists) or dominant negative (antagonists) with respect to all or a portion of the biological activities of a wild-type protein.

In general, the subject recombinant genes are provided in the form of an expression vector comprising the coding sequence operably linked to at least one regulatory element.

In certain instances, the coding sequence of the present invention may be operably linked to an inducible promoter. Several inducible promoter systems have been described, including those controlled by heavy metals (Mayo, K. E. et al., *Cell* 29:99–108 (1982)), RU-486, a progesterone antagonist (Wang, Y. et al., *Proc. Natl. Acad. Sci.* (*USA*) 91:8180–8184 (1994)), steroids (Mader & White, *Proc. Natl. Acad. Sci.* (*USA*) 90:5603–560)$_7$ (1993)) and tetracycline (Gossen & Bujard, *Proc. Natl. Acad. Sci.* (*USA*) 89:5547–5551 (1992)).

It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, may also be considered.

The recombinant gene which is employed may result in an intracellular product, i.e., retained in the cell, in the cytoplasm or organelle, e.g., the nucleus, in transport to a membrane, either an intracellular membrane or the cell membrane, or for secretion. In certain embodiments, particularly where the recombinant gene encodes a polypeptide product, it will be desirable for the gene product to be secreted or at least a portion of the protein presented on the extracellular surface of the host cell. Proteins may be directed for secretion by providing the natural secretion signal sequence, if available, or a heterologous secretion signal sequence. In some situations, where the soluble protein of interest is a fragment of a larger protein, it may be necessary to provide a signal sequence with such protein, so that upon secretion and processing at the processing site, the desired protein will have the natural sequence. Examples include growth hormone, Factor VIII, Factor IX, cytokines, angiogenic factors, transforming growth factors (TGFs), antagonists of cytokine receptors, glucose transporters, insulin receptors, contraceptives, or addressins to promote adhesion and migration to specific sites.

The expression vector may also include a marker for selection of host cells which contain the construct, particularly where the subject transfection system is to be used as part of an ex vivo gene therapy protocol. Normally, the marker will allow for positive selection, in providing protection from one or more cytotoxic agents. For example, neomycin resistance may be employed, where the cells may be selected with G418, dihydrofolate reductase may be employed for resistance to methotrexate, the cell sorter may be used to select cells expressing LacZ, and the like. The marker may be an inducible or non-inducible gene, so that selection may occur under induction or without induction.

The vector may also include a replication origin and such other genes which are necessary for replication in the host. The replication system comprising the origin and any proteins associated with replication encoded by the particular virus may be included as part of a construct. Care must be taken in selecting the replication system, so that the genes which are encoded for replication do not provide for transformation of the myoblasts. Illustrative replication systems include Epstein-Barr virus (Margolskee et al., *Mol. Cell. Biol.* 8:2837–2847 (1988)). Alternatively, replication defective vehicles may be employed, particularly replication-defective retroviral vectors. These vectors are described by Price et al., *Proc. Natl. Acad. Sci.* 84:156–160 (1987) and Sanes, et al., *EMBO J.* 5:3133–3142 (1986). The final vehicle construct may have one or more genes of interest. Either a cDNA gene or a chromosomal gene may be employed.

To further illustrate exemplary uses of the subject methods and reagents, the following list indicates various genes of interest and associated diseases, as appropriate, for which the coacervates of the present invention may be employed for gene therapy:

(i) Single Gene Defects:
Factor IX and Factor VIII (hemophilias: clotting disorders)
alpha-1-antitrypsin (emphysema)
growth hormone (inherited and acquired growth hormone deficiency)
adenosine deaminase (other immunodeficiency disorders)
enzyme defects (metabolic disorders)
dystrophin (Duchenne and Becker muscular dystrophy)
(ii) Cancer:
interferon (leukemia)
Interleukin-2 (T-cell activator: leads to tumor shrinkage)
leuprolide:analog of human gonadotropin (ovarian and testicular)
asparaginase (leukemia)
monoclonal antibodies (specific IgG) to specific proteins
granulocyte colony stimulating factor (all cancers: allows higher doses of chemotherapy
(iii) Brain:
glucocerebrosidase (other lysosomal storage disorders; Tay Sachs)
Levodopa (Parkinson's)
nerve growth factor (Alzheimer's)
(iv) Regulated Expression Systems:
insulin (diabetes)
glucose transporter (diabetes)
growth factors: IGF-I and IGF-II
(v) Infectious Diseases:
deliver of antisense sequences, toxin genes, or other genes into cells to interfere with expression of the pathogenic genetic functions
(vi) Contraception:
antibody to human chorionic gonadotropin
antibodies to zona pellucida antigens or sperm antigens
progesterone antagonist
(vii) Pain:
endorphins (dynorphin): endogenous opiates
(viii) Clotting Disorders:
Factor VIII and Factor IX (hemophilias)
tissue plasminogen activator
(ix) Organ and Cell Transplants:
antibody to CD4 (HLA)
(x) AIDS:
growth hormone to stimulate lymphocyte proliferation
CD4 protein as a decoy to keep virus from interacting with CD4 T-cells
(xi) Other:
hormones, serum proteins, other humoral or diffusible proteins, and low, molecular weight metabolic products In yet another embodiment, the subject coacervates may be used to deliver a "gene activation" construct which, by homologous recombination with a genomic DNA, alters the regulatory elements of an endogenous gene. For instance, the gene activation construct may replace the endogenous promoter of a gene with a heterologous promoter, e.g., one which causes constitutive expression of the gene or which causes inducible expression of the gene under conditions different from the normal expression pattern of the gene. A variety of different formats for the gene activation constructs are available. See, for example, PCT publications WO93/09222, WO95/31560, WO96/29411, WO95/31560 and WO94/12650.

In certain embodiments, the nucleotide sequence used as the gene activation construct may be comprised of (i) DNA from some portion of the endogenous gene (exon sequence, intron sequence, promoter sequences, etc.) which direct recombination and (ii) heterologous regulatory element(s) which is to be operably linked to the coding sequence for the genomic gene upon recombination of the gene activation construct.

The gene activation construct is inserted into a cell, and integrates with the genomic DNA of the cell in such a position so as to provide the heterologous regulatory sequences in operative association with the native gene. Such insertion occurs by homologous recombination, i.e., recombination regions of the activation construct that are homologous to the endogenous gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and may facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, may include one or more regulatory elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the *cytomegalovirus* (CMV) promoter/enhancer (Karasuyama et al., *J. Exp. Med.,* 169:13 (1989),), the human β-actin promoter (Gunning et al., *PNAS* 84:4831–4835 (1987)), the glucocorticoid-inducible promoter present in the mouse mammary tumor virus long terminal repeat (MMTV LTR) (Klessig et al., *Mol. Cell Biol.* 4:1354–1362 (1984)), the long terminal repeat sequences of Moloney murine leukemia virus (MuLV LTR) (Weiss et al., *RNA Tumor Viruses* (1985)), the SV40 early or late region promoter (Bernoist et al., *Nature* 290:304–310 (1981); Templeton et al., *Mol. Cell Biol,* 4:817 (1984); and Sprague et al., *J. Virol.,* 45:773 (1983)), the promoter contained in the 3' long terminal repeat of Rous sarcoma virus (RSV) (Yamamoto et al., *Cell,* 22:787–797 (1980)), the herpes simplex virus (HSV) thymidine kinase promoter/enhancer (Wagner et al., *PNAS* 82:3567–71 (1981)), and the herpes simplex virus LAT promoter (Wolfe et al., *Nature Genetics,* 1:379–384(1992)).

In still other embodiments, the replacement region merely deletes a negative transcriptional control element of the native gene, e.g., to activate expression, or ablates a positive control element, e.g., to inhibit expression of the targeted gene.

B. Target Cells

The present invention may be used to introduce exogenous nucleic acid molecules into a variety of cells and tissues including, without limitation, muscle cells, endothelial cells, myeloid cells, bone marrow cells, stem cells (including hematopoietic and embryonic stem cells), lymphocytes, hepatocytes, fibroblasts, lung epithelial cells, embryonic cells, and nerve cells. In certain embodiments, the subject coacervates may be used to transfect muscle or other cells of myocytic lineage.

A salient feature of certain embodiments of the coacervates of the present invention is the property of being able to transduce both proliferating and nonproliferating cells. This ability may be significant advantage of the invention because of the proliferation characteristics of many of the target cells which one would like to transduce in various gene therapy protocols. In particular, many important target cells may alter their properties in undesirable ways when they divide, or they may divide very slowly, or they may not divide at all. Thus, the present invention may be useful in the transduction of such cells as normal muscle cells, normal hepatocytes, hematopoietic stem cells, neurons, quiescent lymphocytes, and normal epithelial cells (where "normal" refers only to the proliferative index of the cells). In terms of clinical practice, the gene delivery systems of the present invention may be useful in the treatment of a broad range of inherited and acquired diseases and medical conditions including, without limitation, hematologic diseases, cardiopulmonary diseases, endocrinological diseases, transplantation associated disorders, autoimmune disorders, neurodegenerative diseases, neoplasias, and the like.

1. Muscle

The subject gene delivery systems may also be used to transduce muscle cells in vitro and in vivo. Muscle is an important target for gene therapy in the treatment of several muscle and nerve diseases. Controlled gene expression in muscle may also be used to express genes that invoke an immune response, as well as to produce sustained levels of proteins that act on systemic disease.

Another reason that muscle may be used as a site for the delivery and expression of poly-nucleotides in a number of therapeutic applications is because animals have a proportionately large muscle mass which is conveniently accessed by direct injection through the skin; for this reason, a comparatively large dose of the subject gene therapy vectors may be deposited in muscle by single or multiple injections, and the nature of the slow-release coacervates may extend the gene therapy over long periods of time.

For instance, muscle disorders related to defective or absent gene products may be treated by introducing expression vectors or other constructs coding for a non-secreted gene product into the diseased muscle tissue. In a another strategy, disorders of other organs or tissues due to the absence of a gene product, and which results in the build-up of a circulating toxic metabolite may be treated by introducing the specific therapeutic polypeptide into muscle tissue where the non-secreted gene product is expressed and clears the circulating metabolite. In yet another strategy, an expression vector or other construct coding for a secretable therapeutic polypeptide may be injected into muscle tissue from where the polypeptide is released into the circulation to seek a metabolic target. In still another embodiment, in immunization strategies, muscle cells may be injected with constructs coding for immunogenic peptides, and these peptides will be presented by muscle cells in the context of antigens of the major histocompatibility complex to provoke a selected immune response against the immunogen.

2. Nucleic Acid Vaccines

In one embodiment, the subject coacervates may be used to form nucleic acid vaccines, e.g., DNA vaccines, for immunization against pathogens, cancer, and the like. DNA vaccination presents a number of features of potential value. Multiple antigens may included simultaneously in the vaccination. Such vaccination may work even in the presence of maternal antibodies.

DNA vaccination may be applied to eliminate or ameliorate existing disease or conditions, including chronic infectious diseases. For instance, the subject DNA vaccines may be used for immunizing subjects against such infections as HSV, HIV, HCV, influenza, malaria, Ebola, hepatitis B, *papillomavirus* and the like. Moreover, the DNA vaccines may also be employed as part of a protocol for induction of tolerance, such as in the treatment of allergies and other autoimmune conditions, such as multiple sclerosis, Type I diabetes, and rheumatoid arthritis.

The goal of vaccination is the induction of protective immunity. The target was once limited to infectious diseases, but has now broadened to include treatment of tumors, allergy, and even autoimmune diseases. The delivery of naked plasmid DNA results in the expression of the encoded antigen by muscle cells, and perhaps APCs, resulting in the induction of protective CTLs as well as antibody responses. This method of "genetic immunization" with polynucleic acid vaccines (PNV) may represent a significant advance in vaccination technology because it may be used repeatedly to immunize to different antigens while avoiding the risk of an infectious virus and the problem of the immune response to the vector.

DNA vaccination using the coacervates of the present invention may produce different results from other vaccination efforts using DNA, such as naked injection of DNA. The pattern of antigen express, both temporally and spatially, may differ from naked injection of DNA.

The coacervates of the present invention may be used to deliver a coding sequence for an antigen(s) as part of a genetic immunization protocol. U.S. Pat. No. 5,783,567 and WO 94/04171 present a number of potential polypeptide sequences for inducing an immunogenic response.

As described in the appended examples, the subject coacervates may elicit a strong immune response even at low dose. The choice of coacervate, along with selection of regulatory elements, may be used to optimize the vaccine response. For example, the coacervate in which the nucleic acid or other material is incorporated, and the constituents of such coacervate or other material encapsulated in the coacervate, may serve as an adjuvant, wherein an "adjuvant" is a substance that in combination with specific antigen may produce more immunity than the antigen alone. The size of any coacervates of the subject invention may affect immunogenicity. Additional adjuvants may be administered to enhance the inherent adjuvant effect of the coacervates.

By controlling the rate of release from the coacervates of the sequence giving rise to the antigen, it may be possible to prepare a single dose vaccine to replace a vaccination protocol requiring an initial vaccination followed by booster doses.

In another aspect of the present invention, a variety of DNA vaccination techniques may be employed with the coacervates of the present invention to elicit a stronger immune response. For example, in certain embodiments, a naked nucleic acid, such as DNA, may be administered along with a coacervate of the present invention loaded with the same nucleic acid or, alternatively, a different nucleic acid or acids (as well as possibly other materials). In this example, the initial dose of naked nucleic acid followed by release of nucleic acid from the coacervate may result in a more effective vaccination.

In one embodiment, the subject method may be used as part of a vaccination against microbial pathogens. A major obstacle to the development of vaccines against viruses and bacteria, particularly those with multiple serotypes or a high rate of mutation, against which elicitation of neutralizing antibodies and/or protective cell-mediated immune responses is desirable, is the diversity of the external proteins among different isolates or strains. Since cytotoxic T-lymphocytes (CTLs) in both mice and humans are capable of recognizing epitopes derived from conserved internal viral proteins (Yewdell et al., *PNAS* 82:1785 (1985); Townsend, et al., *Cell* 44:959 (1986); McMichael et al., *J. Gen. Virol* 67:719 (1986)); Bastin et al., *J. Exp. Med.* 165:1508 (1987); Townsend et al., *Annu. Rev. Immunol.* 7:601 (1989)), and are thought to be important in the immune response against viruses (Lin et al., *J. Exp. Med.* 154:225 (1981); Gardner et al., *Eur. J. Immunol,* 4:68 (1974); Taylor et al., *Immunol,* 58:417 (1986)), efforts have been directed towards the development of CTL vaccines capable of providing heterologous protection against different viral strains.

Those skilled in the art will recognize appropriate epitopes for use generating an immunizing form of the subject coacervates. It is known that CTLs kill virally- or bacterially-infected cells when their T cell receptors recognize foreign peptides associated with MHC class I and/or class II molecules. These peptides may be derived from endogenously synthesized foreign proteins, regardless of the protein's location or function within the pathogen. By recognition of epitopes from conserved proteins, CTLs may provide heterologous protection. In the case of intracellular bacteria, proteins secreted by or released from the bacteria are processed and presented by MHC class I and II molecules, thereby generating T-cell responses that may play a role in reducing or eliminating infection.

In an exemplary embodiment, the subject method may be used to produce a protective vaccination against infection by *Mycobacterium tuberculosis*. Genes encoding *Mycobacterium tuberculosis* proteins may cloned into eukaryotic expression vectors, and formulated into the subject coacervates for expression of the encoded proteins in mammalian muscle cells in vivo.

3. Treatment of Dystrophic Muscle Diseases

Another application of the subject method is in the treatment of muscular dystrophy. The genetic basis of the muscular dystrophies is beginning to be unraveled. The gene related to Duchenne/Becker muscular dystrophy has recently been cloned and encodes a rather large protein, termed dystrophin. An attractive approach would be to directly express the dystrophin gene within the muscle of patients with Duchennes. Because most patients die from respiratory failure, the muscles involved with respiration would be a primary target.

The present gene delivery systems may be used to express high levels of the following genes specifically in muscle tissue; the full length Duchenne's muscular dystrophy gene (dystrophin), the related sequence of the gene responsible for Becker's muscular dystrophy; myotonin protein kinase; alph alpha-subunit of Na+ channels; the 50 kd-dystrophyn associated glycoprotein; myophosphorylase; phosphofructokinase; acid maltase; glycogen debrancing enzyme; phosphoglycerate kinase; phosphoglycerol mutase; lactate dehydrogenase; and carnitine palmitoyl transferase. The appropriate gene for the particular afflicted individual may be determined through genetic screening as known in the art.

4. Treatment of Heart Tissue

In another embodiment, gene transfer into heart tissue using the subject coacervates may be used to treat both genetic and acquired heart disease. There are a variety of diseases and conditions affecting the heart tissue that could benefit from gene therapy.

Pathogenic changes associated with hereditary, environmental and infectious disease may selectively or generally affect the heart endocardium, myocardium, epicardium or pericardium.

The myocardium is an example of a target for gene therapy directed to the heart. The myocardium is the thickest layer of the heart containing the cardiac muscle cells, the impulse-conducting system and connective tissue. Myocardial disease occurs in many forms of heart disease including myocardial infarction, rheumatic heart disease, and hypertensive heart disease. A number of myocardial pathologies involve inflammatory reactions that may impair heart function and persist for long periods of time. Untreated, the inflammatory reaction may produce focal necrosis and compromise cardiac function. In fact, many forms of myocarditis have unknown etiologies. Here the single most apparent symptom upon autopsy is an overwhelming immune response isolated within the cardiac muscle tissue. For these inflammatory diseases, gene therapy may be used to control the immune response. For example, antisense oligonucleotides may be used to control lymphokine release from inflammatory cells.

A construct which is transcribed to an antisense molecule may be designed once a DNA sequence for a particular gene is identified. For example, elevated IL-6 levels are observed both in cardiac inflammation associated with adventitious agents and autoimmune disease. It may therefore be beneficial to deliver IL-6 "antisense construct," e.g., which is transcribed to an antisense RNA which hybridizes to IL-6 mRNA, to control IL-6 release from immune cells within the heart. The cDNA sequence for IL-6 is provided in a publication by Hirano et al. (*Nature* 324:73–76, 1986) and Green et al. review the use and application of antisense polynucleotide to regulate protein expression (*Ann. Rev. Biochem.*

55:569–597, (1986). Tumor necrosis factor (TNF-α) is also implicated in IL-6 production and levels of TNF-α are increased at the site of inflammation. Mechanism to modulate TNF-α expression will prove beneficial for controlling localized immune responses in the heart. The sequence for TNF-α is provided by Pennica et al. (*Nature* 312:724, 1984). Alternatively, transforming growth factor (TGF-β) may be used to limit lymphocyte proliferation. An expression construct encoding a TGF-β protein may be introduced directly into heart cells to produce TGF-β thereby limiting lymphocyte proliferation within a localized area. The cDNA sequence for TGF-β is found in a publication by Derynck et al. (*Nature* 316:701–705, 1985). Similarly other growth factors or regulatory molecules may be used to selectively control other cells involved in the immune response.

If the causative agent for myocarditis is identifiable, then antisense polynucleotides or other regulatory proteins may be injected or introduced into the myocardium to act on that causative agent. These polynucleotide sequences may additionally be combined with sequences that encode polypeptides that control the immune response. Myocarditis is associated with rheumatic fever (Group A Streptococci), diphtheria, typhoid fever, scarlet fever and organisms causing infective endocarditis. Viral disorders causing myocarditis include influenza, poliomyelitis, mumps, measles, Epstein Barr virus, Coxsackie and ECHO viruses. In addition most rickettsial infections also induce some myocardial damage. Parasitic infections that may induce myocarditis and create cardiac abnormalities include Chagas' disease (*Trypanosoma cruzi*), toxoplasmosis and trichinosis. In addition, systemic lupus erythromatosus, scleroderma and generalized hypersensitivity reactions may also induce cardiac inflammation. More rarely, *Mycoplasma pneumoniae* and *Toxoplasma gondii* may induce myocarditis. Those conditions of unknown etiology that affect cardiac tissue include Fiedler's and giant cell myocarditis. These infectious agents induce inflammatory responses that may be controlled by the secretion of immunoregulatory polypeptides encoded by constructs delivered by the subject coacervates.

Primary cardiomyopathies include arrhythmias, emboli valve insufficiency and ventricular obstruction. These pathologies may be either familial or acquired and may be amenable to gene therapy. However, for many of these myopathies, the specific causative agent has not yet been identified. Some myopathies, particularly those characterized by restricted ventricular filling, are primarily due to the overproduction of a given protein and would therefore benefit from gene therapy. For example, endocardial fibroelastosis is characterized by focal or diffuse cartilage-like fibroelastic thickening of the mural endocardium that may extend into the myocardium. The use of polynucleotide sequences, in accordance with the present invention, to control protein secretion would be of value.

Similarly, amyloidosis, the accumulation of amyloid protein, effects the heart and may be controllable by the therapy contemplated herein. Polynucleotide sequences encoding protein associated with amyloidosis are available in the literature and are readily identifiable to those with skill in the art. The introduction of antisense sequences by the subject coacervates to control over-expression of a molecule or alternatively, the introduction of sequences coding for functional protein to correct the defective enzyme or regulatory protein responsible for the overproduction of a particular molecule, could cessate further deposit accumulation.

Some diseases thought to be "connective tissue" diseases also involve the heart. These include Rheumatoid arthritis, Lupus erythematosus, polyarthritis and scleroderma. Elevated levels of IL-6 are observed in systemic lupus erythematosus (SLE). As noted above, antisense directed to IL-6 may be beneficial for controlling localized immune responses within cardiac tissue. In addition, Linker-Israeli et al. (*J. Immunol.* 147:117, 1991) have shown that TNF-α is useful to inhibit immune cell stimulation of SLE cells in vitro. Therefore the invention disclosed herein may additionally comprise the delivery of gene sequences encoding TNF-α (Pennica et al. supra.). The immune response within the heart may be controlled using the methods detailed herein.

Individuals with diabetes develop cardiomyopathies over time. Increased levels of atrial natriuretic peptide (ANP) in RNA is found in the heart tissue of some diabetics. The changes in levels of ANP synthesis occur before cardiomyopathic histological changes. ANP levels are even greater in diabetic conditions combined with hypertension (Drexler et al., *Circulation* 79:620 (1989)). Localized levels of ANP may be reduced through the delivery of polynucleotide directed at limiting ANP synthesis. The particular gene sequence chosen may correct a cellular defect associated with a particular cardiac disease or pathology. The gene sequence could encode a range of molecules as discussed and these molecules may be engineered to be expressed either intracellularly or extracellularly. Further, the polynucleotide may be a regulatory molecule of itself (i.e. anti-sense or the like) or encode regulatory or immunoregulatory molecules. The polynucleotide may additionally encode enzymes, hormones, and growth factors.

Cardiac treatment may be performed either prophylactically or on individuals with known cardiac sequelae. Characteristic symptoms of myocardial malfunction include, but are not limited to, arrhythmias, heart pain, cardiac enlargement, and congestive heart failure (predominantly of the right side).

Infusion of calcitonin gene related peptide, an alternate product in calcitonin synthesis, is beneficial for the treatment of congestive heart failure (Shekhar et al., *Am. J. Cardiol.* 67(8):732–736 (1991). Thus, it is additionally contemplated that the subject method may be used to deliver, to the hearts of those patients with congestive heart failure, expression vectors encoding enzymes involved calcitonin synthesis. Inhibitors of angiotensin to converting enzyme are beneficial in controlling experimental cardiac hypertrophy and congestive heart failure (Soubrier et al., *PNAS* 85:9386 (1988); and Michel, *Eur. Heart J. II Suppl. D:* 17 (1990)). The subject coacervates may be used to deliver a recombinant gene encoding protein, or transcribable into an antisense nucleic acid, which inhibits angiotensin converting enzyme.

In other embodiments, the subject method may be used to cause the ectopic expression of adenosine receptors on the surface of the heart. Adenosine is a chemical produced by the heart that regulates heart function and protects the heart (luring periods of low oxygen supply.

5. Myocytes as a Source of Secreted, Recombinant Proteins

In another embodiment, the subject coacervates may be used to cause the ectopic expression, in myocytic cells, of a gene encoding a secreted protein. For example, the subject method may be used to deliver an expression vector cytokines, growth factors, (e.g., EGF, FGF, etc.), colony stimulating factors, interferons, surface membrane receptors, insulin or the like.

In one embodiment, the subject transfection system may be used as part of a gene therapy protocol in the treatment of inflammatory disorders, lupus and colitis. To illustrate, the coacervates of the present invention may be used to treat certain forms of arthritis by intramuscular gene therapy including ectopic expression of a transforming growth factor (TGF). Song et al., *J Clinical Investigation* 101:12(1998) recently reported that plasmid DNA, injected directly into muscle tissue, encoding transforming growth factor-β suppresses chronic disease in a streptococcal cell wall-induced arthritis model. This procedure was observed to reduce dramatically chronic arthritis symptoms in the joints, and now offers an innovative approach for eventually treating human disease. In this report, researchers tested the TGF plasmid in a rat model for human rheumatoid arthritis. In this model, animals that are injected in the abdomen with a preparation of bacterial cell walls soon develop swollen and inflamed joints in the feet. The acute arthritic phase lasts several days and then develops into a long-term chronic condition that is marked by the erosion of cartilage and bone within the joints. When the animals were intramuscularly injected with TGF-encoding plasmids, a dramatic reduction in disease symptoms in the joints was observed. The number of affected joints and the amount of swelling in the joints were both substantially reduced.

This study also demonstrated that the manner in which the protein was administered to the animals determined whether or not the outcome was favorable. Injecting TGF directly into joints led to a worsening of the condition. On the other hand, injection of the protein into the abdomen or under the skin, which delivers TGF into the blood stream, dramatically improved symptoms. However, this route of delivery also carries the risk of bone marrow suppression, anemia, and formation of fibrous tissues in the kidneys-undesirable side effects associated with exposing the entire body to high levels of TGF. However, using the gene therapy approach rather than administration of the protein permits the production of a low-level supply of TGF that effects the inflammatory response in the joints without disrupting the balance of other bodily functions. The TGF expression system of Song et al., supra, may be adapted for delivery by the coacervates of the present invention.

In another embodiment, the subject coacervates may be used to cause the ectopic expression of an angiogenic growth factor to stimulate the development of collateral arteries, e.g., as part of a "therapeutic angiogenesis" treatment approach. In an exemplary embodiment, the coacervates of the present invention are used to treat ischemic ulcers by ectopic expression of vascular endothelial growth factor (VEGF) in muscle of the afflicted limb.

To illustrate, Baumgartner et al., *Circulation* 97:1114 (1998) reported that preclinical studies have indicated that angiogenic growth factors may stimulate the development of collateral arteries. In that study, naked plasmid DNA encoding the 165-amino-acid isoform of human vascular endothelial growth factor (phVEGF(165)) was injected directly into the muscles of limbs of patients with non-healing ischemic ulcers. The investigators reported newly visible collateral blood vessels, qualitative evidence of improved distal flow in limbs, and marked improvement in healing of ischemic ulcers. The VEGF vectors of Baumgartner et al., supra, may be may be adapted for delivery by the coacervates of the present invention.

In still other embodiments, the subject method may be used for ectopic expression of growth hormone or insulin like growth factor I(IGF-I). Growth hormone is normally produced and secreted from the anterior pituitary and promotes linear growth in prepuberty children. Growth hormone acts on the liver and other tissues to stimulate the production of IGF-I. This factor is, in turn, responsible for the growth promoting effects of growth hormone. Further, this factor serves as an indicator of overall growth hormone secretion. Serum IGF-I concentration increases in response to endogenous and erogenous administered growth hormone. These concentrations are low in growth hormone deficiency. Insulin-like growth factors are one of the key factors that potentiate muscle development and muscle growth. Myoblasts naturally secrete IGF-I/IGF-II as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the IGF-I receptor. The intramuscular delivery of an expression vector containing the sequence for growth hormone or IGF-I may be used to treat growth disorders. Because intramuscular expression using the subject coacervates may lead to expression of the GH or IGF-I product for extended periods of time, the subject method may provide a long-term inexpensive way to increase systemic blood concentration of IGF-I in patients with growth hormone deficiency.

Moreover, growth hormone levels decline with increasing age. The levels in healthy men and women above age of 55 are approximately one third lower than the levels in men and women 18 to 33. This is associated with a decrease in the concentration of IGF-I. The decline in growth hormone and IGF-I production correlate with a decrease in muscle mass, termed senile muscle atrophy, and an increase in adiposity that occur in healthy human subjects. Administering growth hormone three times a week to healthy 61 to 81 year old men who had serum levels below those of healthy younger men increased the serum IGF-I levels to within the range found in young healthy adults. This increase level led to increased muscle mass and strength and reduced body fat. The secretion of growth hormone is regulated by a stimulatory (growth hormone releasing hormone) and an inhibitory (somatostatin) hypothalamic hormone.

The gene delivery systems of the present invention may be used to deliver expression vectors encoding growth hormone, the growth hormone releasing hormone (GHRH), or IGF-I. This versatility is important since the GHRH, GH, and IGF-I, while having equivalent desired effects on muscle mass, may have different side effects or kinetics which may affect their efficacy. The expression of the growth factor releasing hormone might be more advantageous than the expression of either IGF-I or the growth hormone vectors transcripts. Since GHRH is reduced in the elderly it appears to be responsible for the lack of GH secretion rather than the anterior pituitary capability of synthesizing growth hormone, thus the increased expression of GHRH from muscle would increase GHRH levels in the systemic blood system and may allow for the natural diurnal secretion pattern of GH from the anterior pituitary. In this way, GHRH could act as the natural secretagogue, allowing for evaluated secretion or release of GH from the hypothalamus of the elderly.

Thus, the application of coacervates described herein to express insulin-like growth factors through the ectopic expression of IGF-I, HG, or GHRH into adult muscle of the elderly may represent a long-term inexpensive way to increase systemic blood concentration of IGF-I in the elderly.

6. Treatment of Atherosclerotic Cardiovascular Diseases

Atherosclerotic cardiovascular disease is a major cause of mortality in the United States and the world. The atherosclerotic plaque, the basic underlying lesion in atherosclerosis, contains cholesterol esters that are derived from circulating lipids. These circulating lipids are essential to the development of atherosclerosis. The plasma concentration of high density lipoprotein (HDL) is inversely related to the propensity for developing atherosclerosis. In the nascent state, HDL is secreted in the form of discoidal particles. These particles consist of a bilayer of phospholipids onto which the apolipoproteins (ApoA-I, ApoII and E) are embedded. HDL captures cholesterol esters by the action of an enzyme, lecithin-cholesterol acyltransferase. HDL is secreted from the liver, the small intestine and possibly other tissues.

The ApoA-I cDNA is 878 bp and encodes 267 amino acids, including the 24 amino acid propeptide. Increasing the circulating levels of HDL may influence or reverse cholesterol transport, and thus reduce the propensity for forming atherosclerotic plaques. The insertion of the human ApoA-I coding sequences into an expression vector of the present invention may enhance ApoA-I expression following transfection of that vector into skeletal muscle, and may be used to increases the plasma concentration of HDL.

7. Other Tissue

In another embodiment, the subject coacervates may be used as part of a gene therapy protocol of treatment of liver diseases that are, for example, genetically based, as for example Wilson's disease, glycogen storage diseases, urea cycle enzyme defects, and Creigler-Najir disease. For example, the subject gene delivery systems may be used to correct in inherited deficiency of the low density lipoprotein (LDL) receptor, and/or to correct an inherited deficiency of ornithine transcarbamylase (OTC), which results in congenital hyperammonemia.

In another embodiment, the subject coacervates may be used to treat acquired infectious diseases of the liver, such as diseases resulting from viral infection. For example, the vectors may be employed to treat viral hepatitis, particularly hepatitis B or non-A non-B hepatitis. For example, an coacervate of the present invention, containing a gene encoding an antisense gene, could be transduced into hepatocyctes in vivo to inhibit viral replication. In this case, the infectious viral particle, which includes a vector including a structural hepatitis gene in the reverse or opposite orientation, may be introduced into hepatocytes, resulting in production of an antisense gene capable of inactivating the hepatitis virus or its RNA transcripts. Alternatively, the hepatocytes may be transduced with a vector which includes a gene encoding a protein, such as, for example, α-interferon, which may confer resistance to the hepatitis virus.

Crigler-Najjar syndrome is an autosomal recessive disorder which causes severe jaundice in affected children. Mutation of both alleles of the bilirubin gulcuronosyl transferase (BUGT) gene results in an inability to excrete bilirubin, which then accumulates in the body. The resulting jaundice is unremitting, leading inevitably to brain damage (spasticity, deafness, dementia) and death. The genes for human BUGTs have been cloned by others and an animal model of this syndrome is available. The subject coacervates may be used to deliver the human BUGT gene to hepatocytes in vivo. The response to this gene transfer therapy may be easily monitored by measuring the patient's serum bilirubin level.

Correction of the BUGT defect via gene therapy may provide an alternative to transplantation, the only other therapy currently available.

In another embodiment, the subject transfection system may be used to transfect neuronal cells or endothelial cells.

In another embodiment of the present invention, DNA vaccination may use mucosal delivery, which allows for easy administration, reduced side-effects, and the possibility of frequent boosting without requiring trained medical personnel. Mucosal delivery of vaccines appears to be the only effective means of inducing immune responses in the mucosal secretions. In addition, many pathogens enter the body through the mucosal tissues of the gut or the respiratory or genital tracts.

Another application of the subject gene delivery systems is in the treatment of cystic fibrosis. The gene for cystic fibrosis was recently identified (Goodfellow, *Nature,* 341 (6238):102–3 (Sep. 14, 1989); Rommens, J. et al., *Science* 245(4922):1059–1065 (Sep. 8, 1989); Beardsley, T. et al., *Scientific American,* 261(5):28–30 (1989). Significant amelioration of the symptoms may be attainable by the expression of the dysfunctional protein within the appropriate lung cells. The bronchial epithelial cells are postulated to be appropriate target lung cells, and they may be accessible to gene transfer following instillation of genes into the lung. Since cystic fibrosis is an autosomal recessive disorder one may need to achieve only about 5% of normal levels of the cystic fibrosis gene product in order to ameliorate significantly the pulmonary symptoms.

Biochemical genetic defects of intermediary metabolism may also be treated by the subject method. These diseases include phenylketonuria, galactosemia, maple-syrup urine disease, homocystinuria, propionic acidemia, methylmalonic acidemia, and adenosine deaminase deficiency. The pathogenesis of disease in most of these disorders fits the phenylketonuria (PKU) model of a circulating toxic metabolite. That is, because of an enzyme block, a biochemical that is toxic to the body accumulates in body fluids. These disorders are ideal for gene therapy for a number of reasons. First, only 5% of normal levels of enzyme activity may need to be attained in order to clear significantly enough of the circulating toxic metabolite so that the patient experiences significant improvement. Second, the transferred gene may be expressed in a variety of tissues and still be able to clear the toxic biochemical. Similar transfection of pancreatic islet cells utilizing a coacervate described herein may prove useful in the treatment of insulin dependent diabetes mellitus.

Exemplification

The present invention now being generally described, it may be more readily understood by reference to the following examples, which are included merely for purposes of illustration of certain aspects and embodiments of the present invention and are not intended to limit the invention.

1. Material and Methods

A. Cell Lines and Viruses

Ali cell lines described in the text were obtained directly from the American Type Culture Collection (Rockville, Md.) and maintained in DMEM/F12 supplemented with 10% fetal calf serum and 2 mM glutamine without antibiotics. The recombinant adenovirus, AdCMV-luc, containing a luciferase expression cassette within the E1 region was provided by R. Gerard Hertz et al., *Proc. Natl. Acad. Sci. USA* 90, 2812–16 (1993)). Virus production and storage prior to encapsulation were accomplished according to the procedures described in Goldsmith et al. *Human Gene Therapy* 5, 1341–48 (1994).

B. Fluorescent Labeling of Adenovirus

The AdCMV-luc virus was labeled by incubation with a fluorescently tagged antibody directed against a viral capsid protein. Fluorescein isothiocyanate (FITC)-labeled antibody to the adenovirus hexon protein was commercially obtained (anti-adenovirus type 2 hexon, Accurate Chemical and Scientific Corporation, Westbury, N.Y.). Measured amounts of the antibody and the virus were mixed to achieve a 1:1 antibody-adenovirus stoichiometric ratio and allowed to react at room temperature for 30 min. The unbound antibody was removed by dialysis against phosphate buffered saline overnight.

C. Microsphere Synthesis

Microspheres were made by the coacervation of gelatin and alginate in the presence of the recombinant adenovirus. AdCMV-luc ($10^8$ PFU) was mixed with 1 ml of 0.1% sodium alginate solution. One ml of 3.5% gelatin solution was heated to 50° C. and added while gently vortexing the alginate-virus mixture. Under these conditions, a phase separation occurred with the formation of microspheres containing entrapped adenovirus. The microsphere solution was treated with $CaCl_2$ of varying concentrations as indicated in the discussion below for varying amounts of stabilization. The microspheres were then separated from the supernatant by sucrose gradient centrifugation. By quantification of virus remaining in the supernatant, it was estimated that 72–75% of the adenovirus was encapsulated in the microspheres. By quantification of the gelatin remaining in the liquid phase after coacervation, it was estimated that the total mass of microspheres was 6.5 mg±1% for each lot. The microspheres were separated from the sucrose by dialyzing against a 1% mannitol solution for 4 hours and subsequently frozen, lyophilized and stored at 4° C.

2. Physical Characteristics

Microspheres were characterized by electron and confocal microscopy for determination of size, morphology and virus distribution. Microspheres containing FITC-labeled virus, rehydrated in a minimal volume of water, were irradiated by a 488 Å Argon laser and light sectioned by confocal microscopy. Similarly rehydrated microspheres were air dried and examined by scanning electron microscopy (SEM) to characterize the external features of the microspheres. Such evaluations showed that the microspheres were approximately 0.8 $\mu$M to 10 $\mu$M in diameter with viruses substantially evenly distributed throughout.

3. In Vitro Virus Release Assays

Serial sampling of media incubated with the microspheres was performed to assess the time-dependent release of adenovirus from the microspheres. One-third of each lot of the microspheres were hydrated in 3 ml of media (DMEM/F12 supplemented with 10% fetal calf serum, 2 mM glutamine and antibiotics). The microspheres were transferred to microfuge tubes incubated at 37° C. with agitation for the duration of the assay. At each sampling time, as defined in the text, the tubes were centrifuged 300 g at room temperature to pellet the microspheres, the supernatant carefully aspirated and replaced with fresh media. Samples were stored at −70° C. Adenovirus present in each sample was quantified by plaque assay using the methods described in Dion et al., *Gene Therapy* 3, 1021–25 (1996).

4. In Vivo Assessment of Virus Release

The ability of the microspheres to release adenovirus was assessed by quantification of the adenoviral transgene expression in human lung cancer xenografts that had received a single injection of the microspheres. Athymic nude mice were engrafted with the HI299 cell lines by subcutaneous injection ($2 \times 10^6$ cells/injection) into the flanks using the methods described in Dion et al., *Cancer Gene Therapy* 3, 230–37 (1996).

At the time tumors were approximately 10–15 mm in greatest diameter, they were injected with microspheres or free AdCMV-luc by a single intratumoral injection (60 l volume) with a 27 ga. needle. The microspheres were suspended at a concentration of 2 g/l. The free adenovirus was diluted in media to achieve the required concentrations for delivery of $10^5$ or $10^6$ PFU in 60 $\mu$l. Three days after injection, mice were sacrificed and the tumor nodules removed by dissection. Each nodule was weighed, homogenized and the luciferase activity normalized to protein concentration and tumor mass determined using the techniques of Dion et al.

5. Discussion

Three lots of microspheres were made with identical amounts of virus, alginate and gelatin, followed by different calcium cross-linking conditions for stabilization. In these assays, all three lots of spheres released significant amounts of virus at the initial 30 minute sampling point. Microspheres stabilized with 3.0% or 1.5% calcium had a similar release profile, in contrast to those stabilized with 0.75%. Microspheres that were stabilized with 3% and 1.5% calcium had similar release curves that showed a sustained release of adenovirus over the first 3.5 hours. The 0.75% stabilized spheres released minimal, additional amounts of virus beyond the 30 minute sampling point. The pattern of release in the 3.0% and 1.5% microspheres was similar; however, the total amount of virus released varied between these two lots. The 3.0% microspheres released a total of $2.4 \times 10^6$ PFU/mil over the entire assay period, compared to the 1.5% lot that released a total of $15.0 \times 10^6$ PFU/ml. The 0.75% lot released a total of $4.5 \times 10^6$ PFU/ml. As shown in the Examples, human lung cancer xenografts had luciferase activity following intratumoral administration of the microspheres containing the AdCMV-luc. The xeno grafts were produced by engrafting the non-small cell lung cancer cell line, HI299, into the flanks of nude mice to form tumor nodules. Either microspheres incorporating adenovirus prepared according to the invention of free adenoviruses were administering by a single intratumoral injection into each nodule. The relative gene transfer accomplished by the microspheres and by the free adenovirus was estimated by quantification of luciferase activity. This analysis showed that the nodules treated with the microspheres had luciferase activities that were significantly greater than those with $10^5$ PFU of free virus (p<0.04), and insignificantly different from the nodules treated with $10^6$ PFU of free virus (p<0.56).

In accordance with the present invention, bioactive recombinant adenovirus was encapsulated in, and subsequently released from, coacervate microspheres composed of gelatin and alginate. The confocal microscopic characterization of the microspheres made with tagged adenovirus showed that virus was present in a relatively homogeneous distribution within the spheres, and in vitro release studies with the microspheres showed is time-dependent release of virus.

The microspheres were subjected to sucrose gradient centrifugation and dialysis prior to lyophilization so that free adenovirus would be unlikely to be present in the final, lyophilized preparations. Thus, it is unlikely that the sustained release observed in the microsphere formulations tested was due to free virus.

The results of the in vitro assays suggest that the adenovirus tolerated the encapsulation conditions with minimal loss of bioactivity. In the microspheres stabilized with 1.5% calcium, the virus released was $1.5 \times 10^7$ PFU/ml over 48 hrs. with a total assay volume of 3 mls to achieve a total of $4.5 \times 10^7$ PFU. It was estimated that approximately $2.5 \times 10^7$ PFUs were encapsulated in each aliquot of the spheres tested in the release assays. This finding strongly suggests that the process of microsphere synthesis and lyophilization did not significantly reduce the viral bioactivity.

The choice of coacervate microsphere formulation containing alginate and gelatin was based in part on the gentle conditions required for microsphere formation prior to lyophilization.

The virus-loaded microsphere according to the invention may be lyophilized after they are produced. Preliminary experiments demonstrated that lyophilization of free adenovirus resulted in a major loss of adenovirus bioactivity. However, it was unexpectedly found that lyophilization of the virus within the microsphere greatly minimized the bioactivity loss.

As stated above, microspheres prepared according to the invention are capable of sustained or controlled release of the viral vector at a target site. As shown in the Examples, the amount of microspheres administered were estimated to have $1.4 \times 10^6$ PFU which resulted in an estimated gene transfer efficiency that was comparable to the tumors treated with $10^6$ PFU alone.

REFERENCES

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Patents and Patent Applications:
U.S. Pat. No. 4,794,000
U.S. Pat. No. 5,051,304
U.S. Pat. No. 5,256,765
U.S. Pat. No. 5,585,050
U.S. Pat. No. 5,620,883
U.S. Pat. No. 5,643,605
U.S. Pat. No. 5,654,008
U.S. Pat. No. 5,686,113
U.S. Pat. No. 5,759,582
U.S. Pat. No. 5,807,757
U.S. Pat. No. 5,834,271
U.S. Pat. No. 5,861,159
EP 0 256 856
EP 0 273 823
EP 0 274 431

PUBLICATIONS AND OTHER REFERENCES

Abdallah et al., *Biol. Cell* 85:1–7 (1995)
Alexakis et al., *Applied Biochemistry and Biotechnology* 50:93–106 (1995)
Beer et al., *Advanced Drug Delivery Review* 27:59–66 (1997)
Crystal, *Nature Medicine* 1:15–17 (1995)
Culver et al., *Science* 256:1550–52 (1992)
Deasy et al., *Microencapsulation and Related Drug Process* (Marcel Dekker, New York, 1964)
Diamandis et al., *Clinical Chemistry* 37:625–636 (1991)
Dion et al., *Virology* 231:201–09 (1997)
Felgner, *Advanced Drug Delivery Reviews* 5:163–187 (1990)
Florence et al., *Physicochemical Principles of Pharmacy* (2nd Ed., MacMillan Press, 1988) Chapter 8.
Frechet, *Science* 263:1710–1714 (1994)
Friedmann, *Science* 244:1275–1281 (1989)
Langer, *Science* 249:1527–1533 (1990)
Langer et al., *Science* 260:920–926 (1993)
Ledley, *Human Gene Therapy* 6:1129–1144 (1995)
Leong et al., *Journal of Controlled Release* 53:183–193 (1998)
Miller, *Nature* 357:455–460 (1992)
Mulligen, *Science* 260:926–932 (1993)
Payne et al., *Advances in Mucosal Immunology* (Mestecky, et al., eds., Plenum Press, New York) 1475–80 (1995)
Peppas et al., *Science* 263:1715–1720 (1994)
Ratner, *Journal of Molecular Recognition* 9:617–625 (1996).
Truong-Le et al., *Archives of Biochemistry and Biophysics* 361:47–56 (1999)
Truong-Le et al., *Human Gene Therapy* 9:1709–1717 (1998)
Truong-Le et al., *Drug Delivery* 2:166–74 (1995)
Smith et al., *Advanced Drug Delivery Reviews* 26:135–150 (1997)
Wang et al., *Proc. Natl. Acad. Sci.* 84:7851–7855 (1987)
Wang et al., *Biochemistry* 28:9508–9514 (1989)
Wilson, *Nature* 365:691–692 (1993)

Equivalents

Those skilled in the art will be able to ascertain many equivalents to those certain embodiments described herein. Such equivalents are intended to be included within the scope of the following claims.

What is claimed is:

1. A composition for controlled release of a nucleic acid, comprising:
   a. a coacervate microsphere crosslinked by a crosslinked agent comprising a metal cation;
   b. a nucleic acid incorporated in said coacervate microsphere; and
   c. a delivery agent incorporated in said coacervate microsphere,
wherein the coacervate microsphere comprises a polycationic molecule and a polyanionic molecule other than said nucleic acid and the delivery agent is other than said polycationic molecule of the coacervate microsphere.

2. The composition of claim 1, wherein said nucleic acid is a transfer vector.

3. The composition of claim 2, wherein said transfer vector includes a transgene.

4. The composition of claim 2, wherein said delivery agent is at least one of the following: amphiphilic molecule, lipid or polylysine.

5. The composition of claim 1, wherein said metal cation comprises calcium.

6. The composition of claim 1, wherein said polyanionic molecule is alginate.

7. The composition of claim 1, wherein said polycationic molecule is gelatin.

8. The composition of claim 1, wherein said polycationic molecule is gelatin, and wherein said polyanionic molecule is alginate.

9. The comparison of claim 2, wherein said transfer vector comprises at least one regulatory element.

10. The composition of claim 9, wherein said regulatory element is a promoter.

11. The composition of claim 2, wherein said transfer vector comprises an expression vector.

12. The composition of claim 2, wherein said transfer vector comprises a viral vector, said delivery agent is a virus, and said virus comprises at least about five percent by weight of said microsphere.

13. The composition of claim 11, wherein said microsphere, when administered to a target cell, provides controlled release of said expression vector.

14. The composition of claim 13, wherein said delivery agent facilitates intracellular delivery of said expression vector in said target cell.

15. The composition of claim 14, wherein said expression vector produces a recombinant protein in said target cell.

16. The composition of claim 2, wherein said microsphere is lyophilized.

17. The composition of claim 13, wherein said microsphere further comprises a second expression vector.

18. The composition of claim 1, wherein said nucleic acid is a viral vector, and said delivery agent is a virus.

19. The composition of claim 1, wherein said delivery agent is a virus, a viral particle or a viral vector.

20. The composition of claim 19, wherein said viral vector contains a transgene.

21. The composition of claim 19, wherein said viral vector contains a nucleic acid encoding a recombinant gene product.

22. The composition of claim 19, wherein said viral vector, said virus and said viral particle are obtained from one of the following: recombinant retrovirus, *adenovirus*, adeno-associated virus, or herpes simplex virus-1.

23. A gene delivery system for transducing cells, comprising: a coacervate microsphere crosslinked by a crosslinking agent comprising a metal cation that encapsulates at least a nucleic acid and a delivery agent that is other than a polycation of the coacervate microsphere, for facilitating intracellular delivery of said nucleic acid, wherein upon contact of cells with said coacervate microsphere, controlled release of said nucleic acid results in transduction of the cells by said nucleic acid, and wherein the coacervate microsphere comprises a polycationic molecule and a polyanionic molecule other than said nucleic acid.

24. A method for delivering a nucleic acid into a target cell, comprising: contacting the target cell with a composition comprising a coacervate microsphere crosslinked by a crosslinking agent comprising a metal cation, wherein:
   i. said coacervate microsphere incorporates a nucleic acid contained in a transfer vector having at least one regulatory element;
   ii. said coacervate microsphere comprises a polycationic molecule and a polyanionic molecule other than said nucleic acid; and,
   iii. said coacervate microsphere incorporates a delivery agent,
wherein said contacting of a cell with said composition results in controlled release of said transfer vector in the target cell.

25. The method of claim 24, wherein said transfer vector is a viral vector, said delivery agent is a virus of said viral vector, and said viral vector is enveloped in said virus.

26. The method of claim 25, wherein the nucleic acid encodes a bioactive protein.

27. The method of claim 25, wherein said virus facilitates intracellular delivery of said viral vector.

28. A kit containing a gene delivery system, comprising coacervate microspheres crosslinked by a crosslinking agent comprising a metal cation and instructions for using said microspheres, wherein said microspheres are comprised of a polycationic molecule and a polyanionic molecule, and said microspheres encapsulate a virus.

29. A coacervate microsphere for sustained release of a virus, comprising: a coacervate of gelatin and alginate crosslinked by a crosslinking agent comprising a metal cation and having a virus incorporated therein.

30. The coacervate microsphere of claim 29, wherein said virus comprises a recombinant virus.

31. A method for the sustained release of a virus to a target site, comprising: providing to the target site a coacervate microsphere comprising a coacervate of gelatin and alginate wherein said coacervate microsphere is crosslinked by a crosslinking agent comprising a metal cation and has a virus incorporated therein.

32. A method for preparing a gene delivery system, comprising:
   a. preparing a first solution of polycationic molecules and a second solution of polyanionic molecules;
   b. adding to either said first solution or said second solution a nucleic acid; and adding to either said first solution or said second solution a delivery agent;
   c. combining said first solution and said second solution to form a third solution comprising the nucleic acid and the delivery agent; and,
   d. isolating coacervate microspheres formed from a portion of said polycationic molecules and a portion of said polyanionic molecules from said third solution and treating said coacervate microsphere with a metal cation,
wherein said coacervate microspheres encapsulate at least a portion of said nucleic acid and said delivery agent and said coacervate microspheres are crosslinked by a crosslinking agent comprising a metal cation.

33. The method of claim 32, wherein said delivery agent comprises a virus particle including said nucleic acid.

34. The method of claim 32, further comprising mixing said third solution to form said coacervate microspheres.

35. The method of claim 32, wherein said first and said second solution are substantially aqueous.

36. The method of claim 32, further comprising preparing said microspheres for administration to a host, wherein preparing said microspheres does not impair the controlled release of said virus particle from said microspheres.

37. The method of claim 32, further comprising lyophilizing said microspheres after said isolation.

38. A coacervate microsphere for transfection and expression of a recombinant protein prepared by the process comprising:
   a. in any order:
      i. adding a polycationic molecule to a first aqueous solution;
      ii. adding a polyanionic molecule to a second aqueous solution; and,
      iii. adding to either said first or said second solution a virus comprising a viral vector comprising a nucleic acid encoding a recombinant protein and at least one regulatory element;
   b. mixing said first and second solution together to form a coacervate microsphere of said polycationic molecule and said polyanionic molecule encapsulating said virus; and,
   c. isolating said coacervate microsphere and treating said coacervate microsphere with a metal cation,
wherein said coacervate microsphere is crosslinked by a crosslinking agent comprising a metal cation and releases said virus in vivo or in vitro, whereby said virus transfects cells, resulting in expression of said recombinant protein.

39. A gene delivery system for transfecting a cell with a viral vector, comprising:
   a. encapsulation means for encapsulating a viral vector;
   b. delivery means for facilitating intracellular delivery of said encapsulated viral vector;
wherein said encapsulation means comprises a coacervate microsphere comprising a polycation and a polyanion crosslinked by a crosslinking agent comprising a metal cation, and wherein release of said encapsulated viral vector from said encapsulation means transfects a cell.

40. The composition of claim 1, wherein the nucleic acid encodes a polypeptide which inhibits cell proliferation.

41. A method for the sustained release of a virus to a cancer cell, comprising providing said cancer cell with a coacervate microsphere comprising a coacervate microsphere of gelatin and alginate, crosslinked by a crosslinking agent comprising a metal cation and having a virus incorporated therein.

* * * * *